(12) United States Patent
Wilton et al.

(10) Patent No.: US 10,376,536 B2
(45) Date of Patent: Aug. 13, 2019

(54) MULTIPLE SCLEROSIS TREATMENT

(71) Applicant: MURDOCH UNIVERSITY, Murdoch (AU)

(72) Inventors: Stephen Donald Wilton, Applecross (AU); Sue Fletcher, Bayswater (AU); May Aung-Htut, Willetton (AU)

(73) Assignee: MURDOCH UNIVERSITY, Murdoch (AU)

( * ) Notice: Subject to any disclaimer, the term of this patent is extended or adjusted under 35 U.S.C. 154(b) by 0 days.

(21) Appl. No.: 15/573,184

(22) PCT Filed: May 10, 2016

(86) PCT No.: PCT/AU2016/000158
§ 371 (c)(1),
(2) Date: Nov. 10, 2017

(87) PCT Pub. No.: WO2016/179634
PCT Pub. Date: Nov. 17, 2016

(65) Prior Publication Data
US 2018/0104273 A1 Apr. 19, 2018

(30) Foreign Application Priority Data
May 11, 2015 (AU) .............................. 2015901703

(51) Int. Cl.
C12N 15/11 (2006.01)
C12N 15/113 (2010.01)
A61K 31/7105 (2006.01)
A61K 48/00 (2006.01)

(52) U.S. Cl.
CPC ........ *A61K 31/7105* (2013.01); *A61K 48/005* (2013.01); *C12N 15/111* (2013.01); *C12N 15/113* (2013.01); *C12N 2310/11* (2013.01); *C12N 2320/33* (2013.01)

(58) Field of Classification Search
CPC .............. C12N 15/113; C12N 2310/11; C12N 2310/32; C12N 2310/33; A01K 2207/05; A61K 31/712
See application file for complete search history.

(56) References Cited

U.S. PATENT DOCUMENTS

| 4,458,066 | A | 7/1984 | Caruthers et al. | |
|---|---|---|---|---|
| 5,149,797 | A | 9/1992 | Pederson et al. | |
| 5,968,826 | A * | 10/1999 | Bennett | C12N 15/1138 |
| | | | | 435/325 |
| 6,287,860 | B1 | 9/2001 | Monia et al. | |
| 6,806,084 | B1 | 10/2004 | Debs et al. | |
| 6,887,906 | B1 | 5/2005 | Teng et al. | |
| 6,965,025 | B2 | 11/2005 | Gaarde et al. | |
| 6,969,400 | B2 | 11/2005 | Rhee et al. | |
| 2003/0027780 | A1 | 2/2003 | Hardee et al. | |
| 2004/0248833 | A1 | 12/2004 | Emanuele et al. | |
| 2008/0113351 | A1 * | 5/2008 | Naito | A61K 31/713 |
| | | | | 435/6.11 |
| 2009/0029931 | A1 * | 1/2009 | Tachas | A61K 31/711 |
| | | | | 514/44 R |
| 2010/0016215 | A1 | 1/2010 | Moulton et al. | |
| 2012/0135912 | A1 * | 5/2012 | Paidhungat | C07K 14/70542 |
| | | | | 514/1.1 |
| 2014/0364483 | A1 * | 12/2014 | Lee | C07K 14/47 |
| | | | | 514/44 A |

FOREIGN PATENT DOCUMENTS

| WO | WO-2000/020635 A1 | 4/2000 |
|---|---|---|
| WO | WO-2004/094636 A1 | 11/2004 |
| WO | WO-2005/072340 A2 | 8/2005 |
| WO | WO-2011/143274 A1 | 11/2011 |
| WO | WO-2014/201560 A1 | 12/2014 |

OTHER PUBLICATIONS

U.S. Appl. No. 09/315,298, Teng et al.
Aartsma-Rus et al., Antisense-mediated exon skipping: a versatile tool with therapeutic and research applications, *RNA* 13:1609-24 (2007).
Anderson, Human gene therapy, *Science* 256(5058):808-13 (1992).
Barteau et al., Physicochemical parameters of non-viral vectors that govern transfection efficiency, *Curr Gene Ther*. 8(5):313-23 (2008).
Beaucage et al., Deoxynucleoside phosphoramidites—A new class of key intermediates for deoxypolynucleotide synthesis, *Tetrahedron Letters* 22:1859-62 (1981).
Canocio et al., Expression of a CMV Promoter Driven Human a-1 Antitrypsin Gene in Cultured Lung Endothelial Cells and in the Lungs of Rabbits, Clinical Research, 39(2):2019 (1991).
Brigham et al., In vivo transfection of murine lungs with a functioning prokaryotic gene using a liposome vehicle, *Am. J. Med. Sci.* 298:278-81 (1989).
Cooper et al., Single section Western blot: improving the molecular diagnosis of the muscular dystrophies, *Neurology* 61:93-7 (2003).
Devereux et al., A comprehensive set of sequence analysis programs for the VAX, *Nucleic Acids Research* 12:387-95 (1984).
Fraley et al., New generation of liposomes. The engineering of an efficient vehicle for intracellular delivery of nucleic acids, *Trends Biochem. Sci.* 6:77-80 (1981).
Friedmann, Progress toward human gene therapy, *Science* 244:1275-80 (1989).
Gebski et al., Morpholino antisense oligonucleotide induced dystrophin exon 23 skipping in mdx mouse muscle, *Human Molecular Genetics* 12(15):1801-11 (2003).
Hazinski et al., Localization and induced expression of fusion genes in the rat lung, *Am. J. Resp. Cell Molec. Biol.* 4:206-9 (1991).
Jearawiriyapaisarn et al., Sustained dystrophin expression induced by peptide-conjugated morpholino oligomers in the muscles of mdx mice, *Mol. Ther.* 16(9):1624-9 (2008).

(Continued)

*Primary Examiner* — Brian Whiteman
(74) *Attorney, Agent, or Firm* — Marshall, Gerstein & Borun LLP

(57) ABSTRACT

An antisense oligomer capable of binding to a selected target on the ITGA4 gene transcript to modify pre-mRNA splicing in an ITGA4 gene transcript or part thereof.

14 Claims, 7 Drawing Sheets

Specification includes a Sequence Listing.

(56) References Cited

OTHER PUBLICATIONS

Li et al., Gene therapy progress and prospects: non-viral gene therapy by systemic delivery, *Gene Ther.* 13(18):1313-9 (2006).

Limmroth et al., CD49d antisense drug ATL1102 reduces disease activity in patients with relapsing-remitting MS, *Neurology* 83(20):1780-8 (2014).

Mann et al., Antisense-induced exon skipping and synthesis of dystrophin in the mdx mouse, *Proc. Natl. Acad. Sci. USA* 98(1):42-7 (2001).

Mannino et al., Liposome mediated gene transfer, *Biotechniques* 6(7):682-90 (1988).

Martin, Remington's Pharmaceutical Sciences, 18th Ed. Mack Publishing Co., Easton, PA, 1435-1712 (1990).

Mueller et al., Gene therapy for cystic fibrosis, *Clin. Rev. Allergy Immunol.* 35(3):164-78 (2008).

Nabel et al., Site-specific gene expression in vivo by direct gene transfer into the arterial wall, *Science* 249:1285-8 (1990).

Rosenberg, Immunotherapy and gene therapy of cancer, *Cancer Research* 51(18):suppl.5074S-9S (1991).

Rosenfeld et al., Adenovirus-mediated transfer of a recombinant alpha 1-antitrypsin gene to the lung epithelium in vivo, *Science* 252:431-4 (1991).

Rosenfeld et al., In vivo transfer of the human cystic fibrosis transmembrane conductance regulator gene to the airway epithelium, *Cell* 68:143-55 (1992).

Simoes et al., Cationic liposomes for gene delivery, *Expert Opin Drug Deliv.* 2(2):237-54(2005).

Summerton et al., Morpholino antisense oligomers: design, preparation, and properties, *Antisense Nucleic Acid Drug Development* 7(3):187-95 (1997).

Villegas et al., Establishment and culture of human skin fibroblasts, *Curr. Proc. Mol. Biol.* 28:28.3 (2005).

Wang et al., pH-sensitive immunoliposomes mediate target-cell-specific delivery and controlled expression of a foreign gene in mouse, *Proc. Natl. Acad. Sci. USA*, 84(22):7851-5 (1987).

Wolff et al., Direct gene transfer into mouse muscle in vivo, *Science* 247(4949):1465-8 (1990).

Wu et al., Receptor-mediated gene delivery and expression in vivo, *J. Biol. Chem.* 263(29):14621-4 (1988).

International Preliminary Report on Patentability, PCT/AU2016/000158, dated Nov. 14, 2017.

International Search Report and Written Opinion of the International Search Authority, PCT/AU2016/000158, dated Jul. 26, 2016.

\* cited by examiner

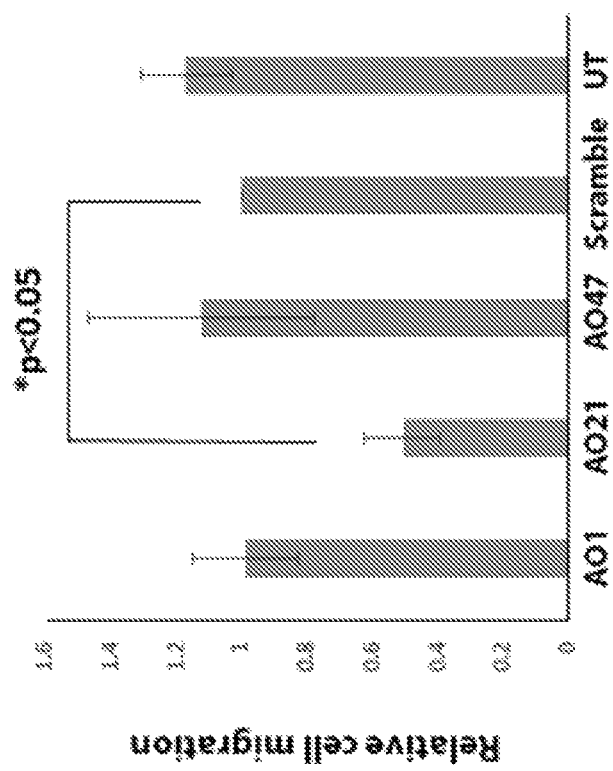

MULTIPLE SCLEROSIS TREATMENT

TECHNICAL FIELD

The present invention relates to antisense oligomers to facilitate splice modification and induce exon skipping in the integrin alpha-4 (ITGA4) gene. The invention further provides methods to treat, prevent or ameliorate the effects of multiple sclerosis by administration of antisense oligomers and therapeutic compositions comprising antisense oligomers to the integrin alpha-4 (ITGA4) gene.

BACKGROUND ART

The following discussion of the background art is intended to facilitate an understanding of the present invention only. The discussion is not an acknowledgement or admission that any of the material referred to is or was part of the common general knowledge as at the priority date of the application.

Multiple Sclerosis (MS) is a neurodegenerative disease affecting approximately 2.5 million people around the world, with a higher risk in women. It is an autoimmune disease that attacks the protective myelin sheath of the neurons in the Central Nervous System (CNS) and results in inflammation and lesions. Patients with MS show one or more symptoms affecting sensation, movement and strength, and feeling and thinking. Symptoms are variable and some may be hidden for years before being diagnosed. MS can be either relapsing or progressive form and 85% of the patients are in the former condition.

The disease onset is still unclear and there is no cure for MS yet. There are several approved disease modifying drugs to modulate the immune system and decrease the frequency and severity of attacks or relapses. To date, no therapeutic drug is available to stop or reverse neurodegeneration. Of all the anti-inflammatory drugs, humanized monoclonal antibody targeting the adhesion molecule integrin alpha-4 (ITGA4) has shown to be effective in treating Relapsing-Remitting MS (RRMS). However, the side effects associated with the use of monoclonal antibodies such as infusion reaction, hypersensitivity and presence of neutralizing antibodies still persist in patients.

The present invention seeks to provide an alternative method to treat, prevent or ameliorate the effects of multiple sclerosis.

SUMMARY OF INVENTION

Broadly, according to one aspect of the invention, there is provided an isolated or purified antisense oligomer for modifying pre-mRNA splicing in the integrin alpha-4 (ITGA4) gene transcript or part thereof. Preferably, there is provided an isolated or purified antisense oligomer for inducing exon exclusion in the ITGA4 gene transcript or part thereof.

For example, in one aspect of the invention, there is provided an antisense oligomer of 10 to 50 nucleotides comprising a targeting sequence complementary to a region near or within an intron of the ITGA4 gene pre-mRNA.

Preferably, the antisense oligomer is a phosphorodiamidate morpholino oligomer.

Preferably, the antisense oligomer is selected from the group comprising the sequences set forth in Tables 3 to 7.

Preferably, the antisense oligomer is selected from the list comprising: SEQ ID NO: 1-202.

The antisense oligomer preferably operates to induce skipping of one or more of the exons of the ITGA4 gene.

The antisense oligomer of the invention may be selected to be an antisense oligomer capable of binding to a selected ITGA4 target site, wherein the target site is an mRNA splicing site selected from a splice donor site, splice acceptor sites, or exonic splicing elements. The target site may also include some flanking intronic sequences when the donor or acceptor splice sites are targeted.

More specifically, the antisense oligomer may be selected from the group comprising of any one or more of SEQ ID NOs: 1-202 and/or the sequences set forth in Tables 3 to 7, and combinations or cocktails thereof. This includes sequences which can hybridise to such sequences under stringent hybridisation conditions, sequences complementary thereto, sequences containing modified bases, modified backbones, and functional truncations or extensions thereof which possess or modulate pre-mRNA processing activity in an ITGA4 gene transcript In certain embodiments, antisense oligomers may be 100% complementary to the target sequence, or may include mismatches, e.g., to accommodate variants, as long as a heteroduplex formed between the oligonucleotide and target sequence is sufficiently stable to withstand the action of cellular nucleases and other modes of degradation which may occur in vivo. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligonucleotide and the target sequence.

The invention extends also to a combination of two or more antisense oligomers capable of binding to a selected target to induce exon exclusion in an ITGA4 gene transcript, including a construct comprising two or more such antisense oligomers. The construct may be used for an antisense oligomer-based therapy.

The invention extends, according to a still further aspect thereof, to cDNA or cloned copies of the antisense oligomer sequences of the invention, as well as to vectors containing the antisense oligomer sequences of the invention. The invention extends further also to cells containing such sequences and/or vectors.

There is also provided a method for manipulating splicing in an ITGA4 gene transcript, the method including the step of:
  a) providing one or more of the antisense oligomers as described herein and allowing the oligomer(s) to bind to a target nucleic acid site.

There is also provided a pharmaceutical, prophylactic, or therapeutic composition to treat, prevent or ameliorate the effects of a disease related to ITGA4 expression in a patient, the composition comprising:
  a) one or more antisense oligomers as described herein and
  b) one or more pharmaceutically acceptable carriers and/or diluents.

The composition may comprise about 1 nM to 1000 nM of each of the desired antisense oligomer(s) of the invention. Preferably, the composition may comprise about 10 nM to 500 nM, most preferably between 1 nM and 10 nM of each of the antisense oligomer(s) of the invention.

There is also provided a method to treat, prevent or ameliorate the effects of a disease associated with ITGA4 expression, comprising the step of:

a) administering to the patient an effective amount of one or more antisense oligomers or pharmaceutical composition comprising one or more antisense oligomers as described herein.

There is also provided the use of purified and isolated antisense oligomers as described herein, for the manufacture of a medicament to treat, prevent or ameliorate the effects of a disease associated with ITGA4 expression.

There is also provided a kit to treat, prevent or ameliorate the effects of a disease associated with ITGA4 expression in a patient, which kit comprises at least an antisense oligomer as described herein and combinations or cocktails thereof, packaged in a suitable container, together with instructions for its use.

Preferably the disease associated with ITGA4 expression in a patient is multiple sclerosis (MS). The subject with the disease associated with ITGA4 expression may be a mammal, including a human.

Further aspects of the invention will now be described with reference to the accompanying non-limiting examples and drawings.

BRIEF DESCRIPTION OF THE DRAWINGS

In the drawings:

FIG. 4 provides a bar graph showing the effect of treatment with exon skipping antisense oligomers targeting exons 3 (AO1), 4 (AO21) and 19 (AO47) and an oligomer of scrambled sequence (at 100 nM) on cell migration property in normal fibroblasts. The bar graph shows an average cell migration after 8 h of wounding from three experiments performed independently. All data were normalised to the sample treated with scrambled oligomer. The error bar represents SEM. Cells treated with antisense oligomers targeting exon 4 (AO21) shows slower migration than the rest of the samples. $p<0.05$ compared to the scrambled oligomer treated samples.

FIG. 5A is a gel of the changes in ITGA4 transcript analysed by RT-PCR. Full length (FL) and exon deleted (Δ) products of ITGA4 transcript are indicated; Untreated (UT). FIG. 5B is a Western blot of ITGA4 expression. FIG. 5C is flow cytometry of the jurkat cells. Among the PMOs tested, the PMOs H3A (+41+65), H4A (+51+75) and H27A (+20+44) targeting exon 3, 4 and 27 produced >50% of transcripts with the targeted exon being skipped. A significant knockdown of the ITGA4 protein was observed in Western blotting and flow cytometry analysis following treatment with H3A (+41+65) and H4A (+51+75). These result correlate with the transcript analysis. For the cells treated with PMO H27A (+20+44), instead of downregulating ITGA4 expression, increased expression of truncated ITGA4 was observed in Western blotting. However, the flow cytometry analysis shows that cell surface expression of ITGA4 was reduced in these cells, indicating the truncated ITGA4 are accumulating within the cells.

DESCRIPTION OF INVENTION

Detailed Description of the Invention

Figure 1:
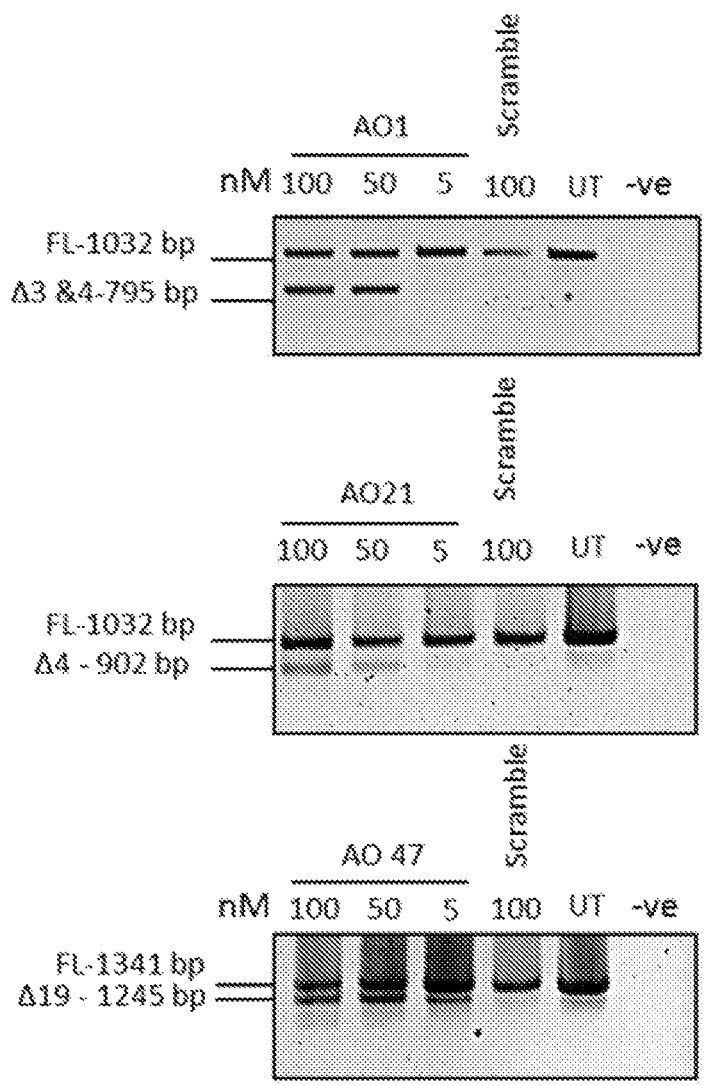
FIG. 1 shows RT-PCR studies indicating changes in the amounts of ITGA4-FL and ITGA4Δ3 and 4 RNA (indicated with arrows) (top panel), ITGA4-FL and ITGA4Δ4 RNA (middle panel) and ITGA4-FL and ITGA4Δ19 RNA (bottom panel) in normal human fibroblasts after transfection with oligomers directed to Exon 3 (antisense oligomer SEQ ID NO: 1), Exon 4 (antisense oligomer SEQ ID NO: 21) and Exon 19 (antisense oligomer SEQ ID NO: 47) at 100, 50 and 5 nM. A clear dose dependent response is seen with antisense oligomer SEQ ID NOs: 1, 21 and 47. An oligomer of scrambled sequence was used as a control (Scrambled antisense oligomer) for non-specific exon skipping.

Integrin alpha-4 is the alpha chain of a hetero-dimeric membrane protein integrin receptor. Together with integrin beta-1, they recognize alternatively spliced CS-1 and CS-5 regions of fibronectin, vascular cell adhesion molecule 1 (VCAM-1) and mucosal vascular addressin cell adhesion molecule 1 (MADCAM-1). Alpha-4/beta-1 integrin (also known as Very Late Antigen (VLA4)) facilitates leucocytes migration across the blood brain barrier through interaction with VCAM-1. The expression level of integrin alpha-4 (ITGA4) has been found to be elevated in MS patients and ITGA4 has been shown to be an effective therapeutic target.

The present invention provides an alternative method for the treatment, prevention or amelioration of the effects of MS by developing antisense oligomers to alter the activity of ITGA4 by reducing the transcripts level through modifying pre-mRNA splicing in the integrin alpha-4 (ITGA4) gene transcript or part thereof.

ITGA4 is encoded by ITGA4 gene located on chromosome 2. It consists of 28 exons and generates 11 transcript variants during RNA maturation and processing. Of these, one transcript codes for a full-length protein and two other transcripts code for truncated proteins. The functional full-length protein contains an extracellular domain encoded by exon 1-26, a trans-membrane domain and a cytoplasmic domain encoded by exon 27 and exon 28 respectively (Table 1).

TABLE 1

A summary of exons encoding for different structures in ITGA4

| Structure | Amino acid no. | | Exon |
|---|---|---|---|
| Topological domain | 35-977 | Extracellular | Ex 1-26 |
| Transmembrane | 978-1001 | Helical | Ex 27 |
| Topological domain | 1002-1032 | Cytoplasmic | Ex 28 |
| Repeat | 35-100 | FG-GAP 1 | Ex 1, 2 |
| Repeat | 110-177 | FG-GAP 2 | Ex 3, 4 |
| Repeat | 185-237 | FG-GAP 3 | Ex 5, 6 |
| Repeat | 238-293 | FG-GAP 4 | Ex 6, 7, 8 |
| Repeat | 294-351 | FG-GAP 5 | Ex 8, 9, 10 |
| Repeat | 355-412 | FG-GAP 6 | Ex 10, 11 |
| Repeat | 416-478 | FG-GAP 7 | Ex 12, 13, 14 |
| Calcium binding | 314-322 | | Ex 9 |
| Calcium binding | 377-385 | | Ex 10 |
| Calcium binding | 439-447 | | Ex 12 |
| Motif | 606-616 | SG1 | Ex 16 |
| Motif | 1003-1007 | GFFKR motif | Ex 28 |

In contrast to other antisense oligomer based therapies, the present invention does not induce increased degradation of RNA via recruitment of RNase H, wherein the RNase H preferentially binds and degraded RNA bound in duplex to DNA of the ITGA4 gene. Nor does it rely on hybridization of the antisense oligomer to the ITGA4 genomic DNA or the binding of antisense oligomers to mRNA to modulate the amount of ITGA4 protein produced by interfering with normal functions such as replication, transcription, translocation and translation.

Rather, the antisense oligomers are used to modify pre-mRNA splicing in an ITGA4 gene transcript or part thereof and induce exon "skipping". The strategy preferably reduces total protein expression or generates proteins which lack functional domains involved in cell migration.

According to a first aspect of the invention, there is provided antisense oligomers capable of binding to a selected target on an ITGA4 gene transcript to modify pre-mRNA splicing in an ITGA4 gene transcript or part thereof. Broadly, there is provided an isolated or purified antisense oligomer for inducing targeted exon exclusion in an ITGA4 gene transcript or part thereof.

By "isolated" is meant material that is substantially or essentially free from components that normally accompany it in its native state. For example, an "isolated polynucleotide" or "isolated oligonucleotide," as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

An antisense oligomer can be said to be "directed to" or "targeted against" a target sequence with which it hybridizes. In certain embodiments, the target sequence includes a region including a 3' or 5' splice site of a pre-processed mRNA, a branch point, or other sequences involved in the regulation of splicing. The target sequence may be within an exon or within an intron or spanning an intron/exon junction.

In certain embodiments, the antisense oligomer has sufficient sequence complementarity to a target RNA (i.e., the RNA for which splice site selection is modulated) to block a region of a target RNA (e.g., pre-mRNA) in an effective manner. In exemplary embodiments, such blocking of ITGA4 pre-mRNA serves to modulate splicing, either by masking a binding site for a native protein that would otherwise modulate splicing and/or by altering the structure of the targeted RNA. In some embodiments, the target RNA is target pre-mRNA (e.g., ITGA4 gene pre-mRNA).

An antisense oligomer having a sufficient sequence complementarity to a target RNA sequence to modulate splicing of the target RNA means that the antisense oligomer has a sequence sufficient to trigger the masking of a binding site for a native protein that would otherwise modulate splicing and/or alters the three-dimensional structure of the targeted RNA.

Selected antisense oligomers can be made shorter, e.g., about 12 bases, or longer, e.g., about 50 bases, and include a small number of mismatches, as long as the sequence is sufficiently complementary to effect splice modulation upon hybridization to the target sequence, and optionally forms with the RNA a heteroduplex having a Tm of 45° C. or greater.

Preferably, the antisense oligomer is selected from the group comprising the sequences set forth in Tables 3 to 7.

In certain embodiments, the degree of complementarity between the target sequence and antisense oligomer is sufficient to form a stable duplex. The region of complementarity of the antisense oligomers with the target RNA sequence may be as short as 8-11 bases, but can be 12-15 bases or more, e.g., 10-50 bases, 10-40 bases, 12-30 bases, 12-25 bases, 15-25 bases, 12-20 bases, or 15-20 bases, including all integers in between these ranges. An antisense oligomer of about 16-17 bases is generally long enough to have a unique complementary sequence. In certain embodiments, a minimum length of complementary bases may be required to achieve the requisite binding Tm, as discussed herein.

In certain embodiments, oligonucleotides as long as 50 bases may be suitable, where at least a minimum number of bases, e.g., 10-12 bases, are complementary to the target sequence. In general, however, facilitated or active uptake in cells is optimized at oligonucleotide lengths of less than about 30 bases. For phosphorodiamidate morpholino oligomer (PMO) antisense oligomers described further herein, an optimum balance of binding stability and uptake generally occurs at lengths of 18-25 bases. Included are antisense oligomers (e.g., PMOs, PMO-X, PNAs, LNAs, 2'-OMe) that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 bases.

In certain embodiments, antisense oligomers may be 100% complementary to the target sequence, or may include mismatches, e.g., to accommodate variants, as long as a heteroduplex formed between the oligonucleotide and target sequence is sufficiently stable to withstand the action of cellular nucleases and other modes of degradation which may occur in vivo. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligonucleotide and the target sequence.

Mismatches, if present, are typically less destabilizing toward the end regions of the hybrid duplex than in the middle. The number of mismatches allowed will depend on the length of the oligonucleotide, the percentage of G:C base pairs in the duplex, and the position of the mismatch(es) in the duplex, according to well understood principles of duplex stability. Although such an antisense oligomer is not necessarily 100% complementary to the target sequence, it is effective to stably and specifically bind to the target sequence, such that splicing of the target pre-RNA is modulated.

The stability of the duplex formed between an antisense oligomer and a target sequence is a function of the binding Tm and the susceptibility of the duplex to cellular enzymatic cleavage. The Tm of an oligonucleotide with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide Hybridization Techniques, Methods Enzymol. Vol. 154 pp. 94-107. In certain embodiments, antisense oligomers may have a binding Tm, with respect to a complementary-sequence RNA, of greater than body temperature and preferably greater than about 45° C. or 50° C. Tm's in the range 60-80° C. or greater are also included.

Additional examples of variants include antisense oligomers having about or at least about 70% sequence identity or homology, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity or homology, over the entire length of any of SEQ ID NOS: 1-202.

More specifically, there is provided an antisense oligomer capable of binding to a selected target site to modify pre-mRNA splicing in an ITGA4 gene transcript or part thereof. The antisense oligomer is preferably selected from those provided in Tables 3 to 7.

The modification of pre-mRNA splicing preferably induces "skipping", or the removal of one or more exons or introns of the mRNA. The resultant protein is preferably of a shorter length when compared to the parent full-length ITGA4 protein due to either internal truncation or premature termination. These truncated ITGA4 proteins may be termed isoforms of the full length ITGA4 protein.

The remaining exons of the mRNA generated may be in-frame and produce a shorter protein with a sequence that is similar to that of the parent full length protein, except that it has an internal truncation in a region between the original 3' and 5' ends. In another possibility, the exon skipping may induce a frame shift that results in a protein wherein the first part of the protein is substantially identical to the parent full length protein, but wherein the second part of the protein has a different sequence (eg a nonsense sequence) due to a frame-shift. Alternatively, the exon skipping may induce the production of a prematurely terminated protein due to a disruption of the reading frame and presence of a premature termination of translation.

Skipping individual exons of exons 3-7, 10-15, 17, 18, 20 and 22 will preferably disrupt the reading frame of the ITGA4 transcript. This will lead to increased degradation of RNA through nonsense mediated decay.

Skipping individual exons of exons 2, 8, 9, 16, 19, 21 and 23-17 will preferably keep the reading frame intact. Skipping a combination of exons 3 and 4 will also preferably keep the reading frame intact. This will preferably lead to translation into an internally truncated protein. The truncated protein or ITGA 4 isoform may have a completely ablated function, or may have a reduced function.

TABLE 2

A summary of frameshift exons

| Exon | Frame shift |
|------|-------------|
| 2 | No |
| 3 | Yes |
| 4 | Yes |
| 5 | Yes |
| 6 | Yes |
| 7 | Yes |
| 8 | No |
| 9 | No |
| 10 | Yes |
| 11 | Yes |
| 12 | Yes |
| 13 | Yes |
| 14 | Yes |
| 15 | Yes |
| 16 | No |
| 17 | Yes |
| 18 | Yes |
| 19 | No |
| 20 | Yes |
| 21 | No |
| 22 | Yes |
| 23 | No |
| 24 | No |
| 25 | No |
| 26 | No |
| 27 | No |

Preferably, these truncated, nonsense or prematurely terminated proteins are lacking one or more functional domains involved in the cell migration process. For example, exon 16 encodes a cell adhesion motif and translated proteins lacking this domain may have slow or disrupted cell migration. Exon 27 encodes a transmembrane domain and removing this exon may generate a soluble ITGA4 protein, which could potentially act as a decoy. The truncated, nonsense or prematurely terminated proteins may further lack an attachment or binding site for other factors, removal of which may lead to a reduction in interaction of the ITGA4 protein with relevant pathways. For example, exons 1 to 26 are extracellular and exon 28 is cytoplasmic. Removal of one or more of these exons may remove a binding site.

Alternatively, the removal of one or more exons may lead to misfolding of the ITGA4 protein and a reduction in the ability of the protein to be successfully transported through the membrane.

The presence of internally truncated proteins (ie proteins lacking the amino acids encoded by one or more exons) is preferable. If the ITGA4 protein is knocked out, there may be problems with elevation of ITGA4 transcription as the body tries to compensate for the reduction in the total amount of ITGA4 protein. In contrast, the presence of an internally truncated protein (preferably lacking one or more of the features of the complete ITGA4 protein), should be sufficient to prevent elevated transcription, but still provide a therapeutic advantage due to a reduction in the total amount of functional ITGA4 protein.

The antisense oligomer induced exon skipping of the present invention need not completely or even substantially ablate the function of the ITGA4 protein. Preferably, the exon skipping process results in a reduced or compromised functionality of the ITGA4 protein.

The different isoforms of ITGA4 produced using different skipping strategies could result in proteins with ablated or reduced activity that could preferably be used to treat or prevent different forms of MS. For example, MS may be in the form of relapsing-remitting MS (RRMS), secondary progressive MS (SPMS), primary progressive MS (PPMS) or progressive relapsing MS. There are also many different symptoms and syndromes associated with MS and its progression. Alternative splicing strategies may form truncated proteins or proteins with reduced functions that can be preferably used as treatments for specific aspects, forms or progression of the disease.

The skipping process of the present invention, using antisense oligomers, may skip an individual exon, or may result in skipping two or more exons at once.

The antisense oligomers of the invention may be a combination of two or more antisense oligomers capable of binding to a selected target to induce exon exclusion in an ITGA4 gene transcript. The combination may be a cocktail of two or more antisense oligomers and/or a construct comprising two or more or two or more antisense oligomers joined together.

TABLE 3

SEQ ID listing of antisense oligomers (2'OMe) inducing human ITGA4 Exon 3, 4 and 19 skipping from transcript.

| SEQ ID NO | Co-ordinates | Sequence | Length (bases) | % exon skipped ITGA4 100 nM |
|---|---|---|---|---|
| | Exon 3 | | | |
| 1 | ITGA4.3A (+30+49) | UCU CUC UCU UCC AAA CAA GU | 20 | 52 |
| 2 | ITGA4.3A (+36+55) | UGA UUG UCU CUC UCU UCC AA | 20 | 51 |
| 3 | ITGA4.3A (+41+65) | CCC CAA CCA CUG AUU GUC UCU CUC U | 25 | 46 |
| 4 | ITGA4.3A (+46+70) | GUG ACC CCC AAC CAC UGA UUG UCU C | 25 | 29 |
| 5 | ITGA4.3A (+51+75) | AAA GUG UGA CCC CCA ACC ACU GAU U | 25 | 34 |
| 6 | ITGA4.3D (+1-24) | CUG UGG ACC AGU UCC AAU ACC UAC C | 25 | 34 |
| 7 | ITGA4.3A (+20+39) | CCA AAC AAG UCU UUC CAC AA | 20 | 29 |
| 8 | ITGA4.3A (+31+50) | GUC UCU CUC UUC CAA ACA AG | 20 | 34 |
| 9 | ITGA4.3A (+32+51) | UGU CUC UCU CUU CCA AAC AA | 20 | 25 |
| 10 | ITGA4.3A (+33+52) | UUG UCU CUC UCU UCC AAA CA | 20 | 28 |
| 11 | ITGA4.3A (+34+53) | AUU GUC UCU CUC UUC CAA AC | 20 | 32 |
| 12 | ITGA4.3A (+35+54) | GAU UGU CUC UCU CUU CCA AA | 20 | 40 |
| 13 | ITGA4.3A (+29+48) | CUC UCU CUU CCA AAC AAG UC | 20 | 22 |
| 14 | ITGA4.3A (+28+47) | UCU CUC UUC CAA ACA AGU CU | 20 | 21 |
| 15 | ITGA4 3A (+27+46) | CUC UCU UCC AAA CAA GUC UU | 20 | 20 |
| 16 | ITGA4.3A (+26+45) | UCU CUU CCA AAC AAG UCU UU | 20 | 29 |
| 17 | ITGA4.3A (+25+44) | CUC UUC CAA ACA AGU CUU UC | 20 | 28 |
| | Exon 4 | | | |
| 18 | ITGA4.4A (-19+6) | ACA AGU CUG AAU AAA AUA AAA GUA G | 25 | 21 |
| 19 | ITGA4.4A (+24+48) | AUU UUC AUU CUU UAU GUA AAA UAU A | 25 | 22 |
| 20 | ITGA4.4A (+46+65) | CCA CCA GUG GGG AGC UUA UU | 20 | 15 |
| 21 | ITGA4.4A (+51+75) | UCC AUA GCA ACC ACC AGU GGG GAG C | 25 | 32 |
| 22 | ITGA4.4A (+51+70) | AGC AAC CAC CAG UGG GGA GC | 20 | 27 |
| 23 | ITGA4.4A (+61+80) | GGC ACU CCA UAG CAA CCA CC | 20 | 22 |
| 24 | ITGA4.4D (+7-18) | AUC AAA AUC AUG CCU UAC CUU GAU A | 25 | 20 |
| 25 | ITGA4.4A (+51+74) | CCA UAG CAA CCA CCA GUG GGG AGC | 24 | 37 |
| 26 | ITGA4.4A (+51+73) | CAU AGC ACG CAC CAG UGG GGA GC | 23 | 36 |
| 27 | ITGA4.4A (+51+72) | AUA GCA ACC ACC AGU GGG GAG C | 22 | 34 |
| 28 | ITGA4.4A (+51+71) | UAG CAA CCA CCA GUG GGG AGC | 21 | 36 |
| 29 | ITGA4.4A (+52+71) | UAG CAA CCA CCA GUG GGG AG | 20 | 34 |
| 30 | ITGA4.4A (+53+72) | AUA GCA ACC ACC AGU GGG GA | 20 | 28 |
| 31 | ITGA4.4A (+56+75) | UCC AUA GCA ACC ACC AGU GG | 20 | 31 |
| 32 | ITGA4.4A (+55+74) | CCA UAG CAA CCA CCA GUG GG | 20 | 26 |
| 33 | ITGA4.4A (+50+74) | CCA UAG CAA CCA CCA GUG GGG AGC U | 25 | 31 |
| 34 | ITGA4.4A (+49+73) | CAU AGC AAC CAC CAG UGG GGA GCU U | 25 | 36 |
| 35 | ITGA4.4A (+48+72) | AUA GCA ACC ACC AGU GGG GAG CUU A | 25 | 34 |
| 36 | ITGA4.4A (+47+71) | UAG CAA CCA CCA GUG GGG AGC UUA U | 25 | 33 |
| 37 | ITGA4.4A (+46+70) | AGC AAC CAC CAG UGG GGA GCU UAU U | 25 | 26 |
| 38 | ITGA4.4A (+52+76) | CUC CAU AGC AAC CAC CAG UGG GGA G | 25 | 33 |
| 39 | ITGA4.4A (+53+77) | ACU CCA UAG CAA CCA CCA GUG GGG A | 25 | 32 |
| 40 | ITGA4.4A (+54+78) | CAC UCC AUA GCA ACC ACC AGU GGG G | 25 | 35 |
| 41 | ITGA4.4A (+56+80) | GGC ACU CCA UAG CAA CCA CCA GUG G | 25 | 30 |
| | Exon 8 | | | |
| 42 | ITGA4.8A (-5+20) | UCA AUG CUG AAU AUA UAU GCC UGU A | 25 | 33 |
| 43 | ITGA4.8A (-5+15) | GCU GAA UAU AUA UGC CUG UA | 20 | 44 |
| 44 | 1TGA4.8A (+1+20) | UCA AUG CUG AAU AUA UAU GC | 20 | 34 |
| | Exon 19 | | | |
| 45 | ITGA4.19A (+20+44) | ACG CCA GAG UUA UCU GUG ACU UCA C | 25 | 37 |
| 46 | ITGA4.19A (+25+44) | ACG CCA GAG UUA UCU GUG AC | 20 | 28 |
| 47 | ITGA4.19A (+30+49) | GUA CCA CGC CAG AGU UAU CU | 20 | 40 |

TABLE 4

SEQ ID listing of antisense oligomers (other chemistry) for inducing human ITGA4 Exon 6, 7, 8, 11, 12, 13, 15, 18, 20, 22 skipping from transcript.

| SEQ ID NO | Co-ordinates | Sequence | Length (bases) |
|---|---|---|---|
| | Exon 3 | | |
| 48 | ITGA4.3A (-18+7) | GGG CUA CCU AUA GCA UGU GAA AAU A | 25 |
| 49 | ITGA4.3D (+11-14) | GUU CCA AUA CCU ACC ACG AUG GAU C | 25 |
| 50 | ITGA4.3D (+6-19) | GAC CAG UUC CAA UAC CUA CGA CGA U | 25 |
| | Exon 4 | | |
| 51 | ITGA4.4A (+55+79) | GCA CUC CAU AGC AAC CAC CAG UGG G | 25 |
| | Exon 6 | | |
| 52 | ITGA4.6A (-11+14) | AUC ACA AUU AAA UCC UGU AAG AAA A | 25 |
| 53 | ITGA4.6A (-6+19) | CCC CCA UCA CAA UUA AAU CCU GUA A | 25 |
| 54 | ITGA4.6A (-1+24) | UGG GGC CCC CAU CAC AAU UAA AUC C | 25 |
| 55 | ITGA4.6A (+33+58) | AGA CAA AAA GAG AGC CAG UCC AGU AA | 26 |
| 56 | ITGA4.6D (+20-5) | AGU ACC UAA AUA ACU UCC AAA UUU U | 25 |
| | Exon 7 | | |
| 57 | ITGA4.7A (-16+9) | CUG AAU AUC CUU UAA GAA AAG GGA G | 25 |
| 58 | ITGA4.7D (+18-7) | UUC UUA CCU UAC CAA UCU GCU CAU G | 25 |
| | Exon 8 | | |
| 59 | ITGA4.8A (+21+45) | AUG UAA GAU AUU UAG UUC UUU UUC A | 25 |
| 60 | ITGA4.8D (+15-10) | GAC AUA UUA CCU UUU UAC CUU UCA U | 25 |
| | Exon 11 | | |
| 61 | ITGA4.11A (-2+23) | UUG UGG AGC UCC GAU AGC AAC AUC U | 25 |
| 62 | ITGA4.11A (-2+18) | GAG CUC CGA UAG CAA CAU CU | 20 |
| 63 | ITGA4.11A (+51+73) | CCA UCU GCA CGG CCA UUG UAA AU | 23 |
| 64 | ITGA4.11D (+21-3) | UAC CUG UGA GAA GGU UGA CGA GAU | 24 |
| | Exon 12 | | |
| 65 | ITGA4.12A (-7+18) | CUG AAG UCC UUC AAU UCU CUG AAA A | 25 |
| 66 | ITGA4.12A (+44+69) | AUC AAU UUG UCC UGA UAU AGA CUG UC | 26 |
| 67 | ITGA4.12D (+7-18) | GAU AAA CUA AUU ACU CAC CUA CAU A | 25 |
| | Exon 13 | | |
| 68 | ITGA4.13A (+21+45) | UUA GCA AGA CAG CAG AAU CAG ACC G | 25 |
| 69 | ITGA4.13D (+1-24) | AGC AGU GAA AUA UAU CAG UCU UAC C | 25 |
| | Exon 15 | | |
| 70 | ITGA4.15A (+56+79) | GUU CCA UUA GAA GAG AAA UAG AAU | 24 |
| 71 | ITGA4.15A (+75+98) | UCC UGU AAU CAC GUC AGA AGU UCC | 24 |
| 72 | ITGA4.15D (+18-6) | CAU UAC CCG CAU AAA UGC UUG AUG | 24 |
| 73 | ITGA4.15D (+22-2) | ACC CGC AUA AAU GCU UGA UGU GUU | 24 |
| | Exon 16 | | |
| 74 | ITGA4.16A (+7+32) | UGA AUU GGG GUG AGG AUG UCC CGC AC | 26 |
| 75 | ITGA4.16A (+47+71) | CUG AUG ACA UGA GGA CCA AGG UGG U | 25 |
| 76 | ITGA4.16A (+82+106) | GCU GAA GUG GUG GGA AUU CCU CUG U | 25 |
| 77 | ITGA4.16A (+114+138) | UAU GUC UUU UUC UUU CUU CUG CUG A | 25 |
| 78 | ITGA4.16A (-77-53) | AAA AAA UAA AAC UCC UUU CCU GAA A | 25 |
| 79 | ITGA4.16A (-39-20) | UAU GAA UUA ACA AAA ACA AG | 20 |
| 80 | ITGA4.16D (+3-22) | GAA UAA AGG AAA AUU UUC CUA CUG U | 25 |
| 81 | ITGA4.16D (-38-57) | UUU UAA AAA UUU AGU UAA AU | 20 |
| 82 | ITGA4.16D (-71-90) | ACA UAU AGU UCA CUU CUU CA | 20 |
| | Exon 19 | | |
| 83 | ITGA4.19A (-33-9) | AAA AAU GAA ACA ACU GUU UUG GAC A | 25 |
| 84 | ITGA4.19A (+15+34) | UAU CUG UGA CUU CAC AGU UU | 20 |
| 85 | ITGA4.19A (+31+50) | UGU ACC ACG CCA GAG UUA UC | 20 |
| 86 | ITGA4.19A (+32+51) | UUG UAC CAC GCC AGA GUU AU | 20 |
| 87 | ITGA4.19A (+33+52) | GUU GUA CCA CGC CAG AGU UA | 20 |
| 88 | ITGA4.19A (+34+53) | AGU UGU ACC ACG CCA GAG UU | 20 |
| 89 | ITGA4.19A (+35+54) | AAG UUG UAC CAC GCC AGA GU | 20 |

TABLE 4-continued

SEQ ID listing of antisense oligomers (other chemistry) for inducing human ITGA4 Exon 6, 7, 8, 11, 12, 13, 15, 18, 20, 22 skipping from transcript.

| SEQ ID NO | Co-ordinates | Sequence | Length (bases) |
|---|---|---|---|
| 90 | ITGA4.19D (+13-12) | UGA AAC ACU UAC CCU UGA GAG AUG A | 25 |
| 91 | ITGA4.19A (+37+56) | UCA AGU UGU ACC ACG CCA GA | 20 |
| 92 | ITGA4.19A (+29+48) | UAC CAC GCC AGA GUU AUG UG | 20 |
| 93 | ITGA4.19A (+28+47) | ACC ACG CCA GAG UUA UCU GU | 20 |
| 94 | ITGA4.19A (+27+46) | CCA CGC CAG AGU UAU CUG UG | 20 |
| 95 | ITGA4.19A (+26+45) | CAC GCC AGA GUU AUC UGU GA | 20 |
| Exon 20 | | | |
| 96 | ITGA4.20A (-18+7) | UAU CUA UCU GUA AAA CAC AGA CCA G | 25 |
| 97 | ITGA4.20A (+20+44) | GCU CUG CUG AGU GAG CUC ACA UCC A | 25 |
| 98 | ITGA4.20D (+19-6) | UUA UAC CAG GUA GCA UGC ACU GUG A | 25 |
| Exon 22 | | | |
| 99 | ITGA4.22A (-3+21) | AAU GAA GUU GGG UUU ACA AAC CUG | 24 |
| 100 | ITGA4.22A (+19+41) | CAU CAU UUG AUG CAU ACA CAA AU | 23 |

TABLE 5

SEQ ID listing of antisense oligomers for inducing human ITGA4 Exon 2, 3, 4, 5, 8, 9, 10, 14, 16, 17, 18, 19, 21, 23, 24, 25, 26 and 27 skipping from transcript.

| SEQ ID NO | Co-ordinates | Sequence | Length (bases) |
|---|---|---|---|
| Exon 2 | | | |
| 101 | ITGA4.2A (-5+20) | UGG GCG CAC CCA CUA GGA GCC UAA A | 25 |
| 102 | ITGA4.2D (+21-4) | UCA CCC AGC UGG AGC UGU UCG CAC G | 25 |
| 103 | ITGA4.2D (-49-74) | CAG GAC UUG CCC UAU GGU GGG GUC CA | 25 |
| Exon 5 | | | |
| 104 | ITGA4.5A (-13+12) | UUU UCA CAU AAU CUA AAA UGA AAU A | 25 |
| 105 | ITGA4.5D (+11-13) | UUU GAA CAA UUA CCU UUG UGU AAA | 24 |
| Exon 9 | | | |
| 106 | ITGA4.9A (-6+19) | CUC CAA AGU ACG AUC CAA GCU GUC C | 25 |
| 107 | ITGA4.9A (+90+114) | CAC UCU UCC UUC CUC UCU GAU GGU G | 25 |
| 108 | ITGA4.9D (+14-11) | CUU GGA CAU ACC GAG CCA GAG UUG A | 25 |
| Exon 10 | | | |
| 109 | ITGA4.10A (-5+20) | AUU GCA UUC AUU ACU GCU CCC UAG A | 25 |
| 110 | ITGA4.10D (+22-3) | UAC CUU CAA AGC CAU CAU UGU CAA U | 25 |
| Exon 14 | | | |
| 111 | ITGA4.14A (-10+15) | ACU ACA GGU CUU GUC CUG AGA AGG A | 25 |
| 112 | ITGA4.140 (+12-13) | AGG GCA UAC CCA CCA AUG UAA CCU G | 25 |
| Exon 17 | | | |
| 113 | ITGA4.17A (-10+15) | CCU UGC AAA GUU UAU CUG GAA AUA A | 25 |
| 114 | ITGA4.17A (+30+54) | AAC CUG UAA AUC AGC AGA ACA AUU U | 25 |
| 115 | ITGA4.17D (+20-5) | CUU ACU UCA AAA ACC CAA UCU UUG C | 25 |
| Exon 18 | | | |
| 116 | ITGA4.18A (-9+16) | UUU AUU UUC AUG GGG CCU AAA AAU U | 25 |
| 117 | ITGA4.18A (+30+52) | CAU CAA UGU CUU CAU ACU CCC AA | 23 |
| 118 | ITGA4.18D (+20-5) | CUU ACC AGC UCU AAA AUC UUA AUG A | 25 |
| Exon 21 | | | |
| 119 | ITGA4.21A (-5+20) | CCA UUU CCU CUU CAU UUU CAC UAU A | 25 |
| 120 | ITGA4.21D (+2-23) | AGG AAG CCU UUA UGU CUA CUU ACC C | 25 |

TABLE 5-continued

SEQ ID listing of antisense oligomers for inducing human ITGA4 Exon 2, 3, 4, 5, 8, 9, 10, 14, 16, 17, 18, 19, 21, 23, 24, 25, 26 and 27 skipping from transcript.

| SEQ ID NO | Co-ordinates | Sequence | Length (bases) |
|---|---|---|---|
| Exon 23 | | | |
| 121 | ITGA4.23A (-10+15) | GCC AGU GUU GAU AAC CUG AUA AGA A | 25 |
| 122 | ITGA4.23D (+12-13) | AAU ACA UUU UUA CCU GGA CAU CCA A | 25 |
| Exon 24 | | | |
| 123 | ITGA4.24A (-4+21) | GUG GCA UUC UCC AGU AGU AGU CUA U | 25 |
| 124 | ITGA4.24D (+23-2) | ACC AAU AGC CUC UUA UCA GUC UUG G | 25 |
| Exon 25 | | | |
| 125 | ITGA4.25A (-4+21) | UGG AUC AGC UUU UAU GCA GUA CUU G | 25 |
| 126 | ITGA4.25A (+60+85) | UAU GAA CAC UGG CUU CUU UUC CAC UU | 26 |
| 127 | ITGA4.25D (+10-14) | UUA GAC UUA CUU ACC AUU UCU AAA | 24 |
| Exon 26 | | | |
| 128 | ITGA4.26A (-12+13) | CUG AAG UCU CAU CCU GUU UAA UAA A | 25 |
| 129 | ITGA4.26D (+18-7) | AUC UUA CAU GCG CAA CAU UCU CAU C | 25 |
| Exon 27 | | | |
| 130 | ITGA4.27A (-10+15) | UCC UUC CAG UAG AAC CUA CGU GAG U | 25 |
| 131 | ITGA4.27A (+20+44) | AAA UAA CGU UUG GGU CUU UGA UGA U | 25 |
| 132 | ITGA4.27D (+20-5) | CUU ACC UUC CAC AUA ACA UAU GAG A | 25 |

TABLE 6

SEQ ID listing of antisense oligomers for inducing human ITGA4 Exon 8, 19, 25 and 27 skipping from transcript.

| SEQ ID NO | Co-ordinates | Sequence | Length (bases) | % exon skipping ITGA4 at 100 nM |
|---|---|---|---|---|
| Exon 8 | | | | |
| 133 | H8A (-10+15) | GCU GAA UAU AUA UGC CUG UAA UUA G | 25 | 33 |
| 134 | H8A (-9+16) | UGC UGA AUA UAU AUG CCU GUA AUU A | 25 | 36 |
| 135 | H8A (-8+17) | AUG CUG AAU AUA UGC CUG UAA UU | 25 | 44 |
| 136 | H8A (-7+18) | AAU GCU GAA UAU AUA UGC CUG UAA U | 25 | 36 |
| 137 | H8A (-6+19) | CAA UGC UGA AUA UAU AUG CCU GUA A | 25 | 42 |
| 138 | H8A (-4+21) | AUC AAU GCU GAA UAU AUA UGC CU G | 25 | 40 |
| 139 | H8A (-3+22) | CAU CAA UGC UGA AUA UAU AUG CCU G | 25 | 45 |
| 140 | H8A (-2+23) | UCA UCA AUG CUG AAU AUA UAU GCC U | 25 | 13 |
| 141 | H8A (-1+24) | UUC AUC AAU GCU GAA UAU AUA UGC C | 25 | 42 |
| 142 | H8A (+1+25) | UUU CAU CAA UGC UGA AUA UAU AUG C | 25 | 40 |
| Exon 19 | | | | |
| 143 | H19A (+20+44) | ACG CCA GAG UUA UCU GUG ACU UCA C | 25 | 37 |
| 144 | H19A (+25+44) | ACG CCA GAG UUA UCU GUG AC | 20 | 28 |
| 145 | H19A (+30+49) | GUA CCA CGC CAG AGU UAU CU | 20 | 40 |
| 146 | H19A (+32+49) | GUA CCA CGC CAG AGU UAU | 18 | |
| 147 | H19A (+30+47) | A CCA CGC CAG AGU UAU CU | 18 | |
| Exon 25 | | | | |
| 148 | H25A (+55+80) | ACA CUG GCU UCU UUU CCA CUU UCC AU | 26 | 48 |
| 149 | H25A (+56+81) | AAC ACU GGC UUC UUU UCC ACU UUC CA | 26 | 49 |
| 150 | H25A (+57+82) | GAA CAC UGG CUU CUU UUC CAC UUU CC | 26 | 49 |
| 151 | H25A (+58+83) | UGA ACA CUG GCU UCU UUU CCA CUU UC | 26 | 47 |
| 152 | H25A (+59+84) | AUG AAC ACU GGC UUC UUU UCC ACU UU | 26 | 48 |
| 153 | H25A (+61+86) | AUA UGA ACA CUG GCU UCU UUU CCA CU | 26 | 48 |
| 154 | H25A (+62+87) | GAU AUG AAC ACU GGC UUC UUU UCC AC | 26 | 43 |
| 155 | H25A (+63+88) | GGA UAU GAA CAC UGG CUU CUU UUC CA | 26 | 43 |
| 156 | H25A (+64+89) | UGG AUA UGA ACA CUG GCU UCU UUU CC | 26 | 46 |
| 157 | H25A (+65+90) | UUG GAU AUG AAC ACU GGC UUC UUU UC | 26 | 44 |

TABLE 6-continued

SEQ ID listing of antisense oligomers for inducing human ITGA4 Exon 8, 19, 25 and 27 skipping from transcript.

| SEQ ID NO | Co-ordinates | Sequence | Length (bases) | % exon skipping ITGA4 at 100 nM |
|---|---|---|---|---|
| | Exon 27 | | | |
| 158 | H27A (-15+10) | CCA GUA GAA CCU ACG UGA GUU AAG A | 25 | 28 |
| 159 | H27A (-14+11) | UCC AGU AGA ACC UAC GUG AGU UAA G | 25 | 36 |
| 160 | H27A (-13+12) | UUC CAG UAG AAC CUA CGU GAG UUA A | 25 | 40 |
| 161 | H27A (-12+13) | CUU CCA GUA GAA CCU ACG UGA GUU A | 25 | 41 |
| 162 | H27A (-11+14) | CCU UCC AGU AGA ACC UAC GUG AGU U | 25 | 40 |
| 163 | H27A (-9+16) | GUC CUU CCA GUA GAA CCU ACG UGA G | 25 | 42 |
| 164 | H27A (-8+17) | AGU CCU UCC AGU AGA ACC UAC GUG A | 25 | 44 |
| 165 | H27A (-7+18) | UAG UCC UUC CAG UAG AAC CUA CGU U | 25 | 45 |
| 166 | H27A (-6+19) | GUA GUC CUU CCA GUA GAA CCU ACG U | 25 | 48 |
| 167 | H27A (-5+20) | UGU AGU CCU UCC AGU AGA ACC UAC G | 25 | 44 |
| 168 | H27D (+17-8) | AUG CUU ACC UUC CAC AUA ACA UAU G | 25 | 22 |
| 169 | H27D (+18-7) | UGC UUA CCU UCC ACA UAA CAU AUG U | 25 | 22 |
| 170 | H27D (+19-6) | GCU UAC CUU CCA CAU AAC AUA UGA G | 25 | 34 |
| 171 | H27D (+21-4) | UUA CCU UCC ACA UAA CAU AUG AGA U | 25 | 38 |
| 172 | H27D (+22-3) | UAC CUU CCA CAU AAC AUA UGA GAU C | 25 | 34 |
| 173 | H27D (+23-2) | ACC UUC CAC AUA ACA UAU GAG AUC A | 25 | 37 |
| 174 | H27D (+24-1) | CCU UCC ACA UAA CAU AUG AGA UCA A | 25 | 38 |

TABLE 7

SEQ ID listing of antisense al garners for inducing human ITGA4 Exon 27 skipping from transcript.

| SEQ ID NO | Co-ordinates | Sequence | Length (bases) |
|---|---|---|---|
| 175 | ITGA4 H27A (-5+19) | GUAGUCCUUCCAGUAGAACCUACG | 24 |
| 176 | ITGA4 H27A (-4+19) | GUAGUCCUUCCAGUAGAACCUAC | 23 |
| 177 | ITGA4 H27A (-3+19) | GUAGUCCUUCCAGUAGAACCUA | 22 |
| 178 | ITGA4 H27A (-2+19) | GUAGUCCUUCCAGUAGAACCU | 21 |
| 179 | ITGA4 H27A (-1+19) | GUAGUCCUUCCAGUAGAACC | 20 |
| 180 | ITGA4 H27A (-6+18) | UAGUCCUUCCAGUAGAACCUACGU | 24 |
| 181 | ITGA4 H27A (-6+17) | AGUCCUUCCAGUAGAACCUACGU | 23 |
| 182 | ITGA4 H27A (-6+16) | GUCCUUCCAGUAGAACCUACGU | 22 |
| 183 | ITGA4 H27A (-6+15) | UCCUUCCAGUAGAACCUACGU | 21 |
| 184 | ITGA4 H27A (-6+14) | CCUUCCAGUAGAACCUACGU | 20 |
| 185 | ITGA4 H27A (+20+43) | AAUAACGUUUGGGUCUUUGAUGAU | 24 |
| 186 | ITGA4 H27A (+20+42) | AUAACGUUUGGGUCUUUGAUGAU | 23 |
| 187 | ITGA4 H27A (+20+41) | UAACGUUUGGGUCUUUGAUGAU | 22 |
| 188 | ITGA4 H27A (+20+40) | AACGUUUGGGUCUUUGAUGAU | 21 |
| 189 | ITGA4 H27A (+20+39) | ACGUUUGGGUCUUUGAUGAU | 20 |
| 190 | ITGA4 H27A (+19+44) | AAAUAACGUUUGGGUCUUUGAUGA | 24 |
| 191 | ITGA4 H27A (+18+44) | AAAUAACGUUUGGGUCUUUGAUG | 23 |
| 192 | ITGA4 H27A (+17+44) | AAAUAACGUUUGGGUCUUUGAU | 22 |
| 193 | ITGA4 H27A (+16+44) | AAAUAACGUUUGGGUCUUUGA | 21 |
| 194 | ITGA4 H27A (+15+44) | AAAUAACGUUUGGGUCUUUG | 20 |

TABLE 7-continued

SEQ ID listing of antisense al garners for inducing human ITGA4 Exon 27 skipping from transcript.

| SEQ ID NO | Co-ordinates | Sequence | Length (bases) |
|---|---|---|---|
| 195 | ITGA4 H27A (+21+45) | GAAAUAACGUUUGGGUCUUUGAUGA | 25 |
| 196 | ITGA4 H27A (+22+46) | UGAAAUAACGUUUGGGUCUUUGAUG | 25 |
| 197 | ITGA4 H27A (+23+47) | GUGAAAUAACGUUUGGGUCUUUGAU | 25 |
| 198 | ITGA4 H27A (+24+48) | GGUGAAAUAACGUUUGGGUCUUUGA | 25 |
| 199 | ITGA4 H27A (+19+43) | AAUAACGUUUGGGUCUUUGAUGAUG | 25 |
| 200 | ITGA4 H27A (+18+42) | AUAACGUUUGGGUCUUUGAUGAUGU | 25 |
| 201 | ITGA4 H27A (+17+41) | UAACGUUUGGGUCUUUGAUGAUGUA | 25 |
| 202 | ITGA4 H27A (+16+40) | AACGUUUGGGUCUUUGAUGAUGUAG | 25 |

The invention further provides a method for manipulating splicing in an ITGA4 gene transcript, the method including the step of:

a) providing one or more of the antisense oligomers as described herein and allowing the oligomer(s) to bind to a target nucleic acid site.

According to yet another aspect of the invention, there is provided a splice manipulation target nucleic acid sequence for ITGA4 comprising the DNA equivalents of the nucleic acid sequences selected from the group consisting of SEQ ID NOs: 1-202, and sequences complementary thereto.

Designing antisense oligomers to completely mask consensus splice sites may not necessarily generate a change in splicing of the targeted exon. Furthermore, the inventors have discovered that size or length of the antisense oligomer itself is not always a primary factor when designing antisense oligomers. With some targets such as IGTA4 exon 3, antisense oligomers as short as 20 bases were able to induce some exon inclusion, in certain cases more efficiently than other longer (eg 25 bases) oligomers directed to the same exon.

The inventors have also discovered that there does not appear to be any standard motif that can be blocked or masked by antisense oligomers to redirect splicing. It has been found that antisense oligomers must be designed and their individual efficacy evaluated empirically.

More specifically, the antisense oligomer may be selected from those set forth in Tables 3 to 7. The sequences are preferably selected from the group consisting of any one or more of any one or more of SEQ ID NOs: 1-202, more specifically SEQ ID NOs: 1-132, and combinations or cocktails thereof. This includes sequences which can hybridise to such sequences under stringent hybridisation conditions, sequences complementary thereto, sequences containing modified bases, modified backbones, and functional truncations or extensions thereof which possess or modulate pre-mRNA processing activity in an ITGA4 gene transcript.

The oligomer and the DNA, cDNA or RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or pairing such that stable and specific binding occurs between the oligomer and the DNA, cDNA or RNA target. It is understood in the art that the sequence of an antisense oligomer need not be 100% complementary to that of its target sequence to be specifically hybridisable. An antisense oligomer is specifically hybridisable when binding of the compound to the target DNA or RNA molecule interferes with the normal function of the target DNA or RNA product, and there is a sufficient degree of complementarity to avoid non-specific binding of the antisense oligomer to non-target sequences under conditions in which specific binding is desired, i.e., under physiological conditions in the case of in vivo assays or therapeutic treatment, and in the case of in vitro assays, under conditions in which the assays are performed.

Selective hybridisation may be under low, moderate or high stringency conditions, but is preferably under high stringency. Those skilled in the art will recognise that the stringency of hybridisation will be affected by such conditions as salt concentration, temperature, or organic solvents, in addition to the base composition, length of the complementary strands and the number of nucleotide base mismatches between the hybridising nucleic acids. Stringent temperature conditions will generally include temperatures in excess of 30° C., typically in excess of 37° C., and preferably in excess of 45° C., preferably at least 50° C., and typically 60° C.-80° C. or higher. Stringent salt conditions will ordinarily be less than 1000 mM, typically less than 500 mM, and preferably less than 200 mM. However, the combination of parameters is much more important than the measure of any single parameter. An example of stringent hybridisation conditions is 65° C. and 0.1×SSC (1×SSC=0.15 M NaCl, 0.015 M sodium citrate pH 7.0). Thus, the antisense oligomers of the present invention may include oligomers that selectively hybridise to the sequences provided in Tables 3 to 7, or SEQ ID NOs: 1-202.

It will be appreciated that the codon arrangements at the end of exons in structural proteins may not always break at the end of a codon, consequently there may be a need to delete more than one exon from the pre-mRNA to ensure in-frame reading of the mRNA. In such circumstances, a plurality of antisense oligomers may need to be selected by the method of the invention wherein each is directed to a different region responsible for inducing inclusion of the desired exon and/or intron. At a given ionic strength and pH, the Tm is the temperature at which 50% of a target sequence hybridizes to a complementary polynucleotide. Such hybridization may occur with "near" or "substantial" complementarity of the antisense oligomer to the target sequence, as well as with exact complementarity.

Typically, selective hybridisation will occur when there is at least about 55% identity over a stretch of at least about 14 nucleotides, preferably at least about 65%, more preferably at least about 75% and most preferably at least about 90%, 95%, 98% or 99% identity with the nucleotides of the antisense oligomer. The length of homology comparison, as described, may be over longer stretches and in certain embodiments will often be over a stretch of at least about nine nucleotides, usually at least about 12 nucleotides, more usually at least about 20, often at least about 21, 22, 23 or 24 nucleotides, at least about 25, 26, 27 or 28 nucleotides, at least about 29, 30, 31 or 32 nucleotides, at least about 36 or more nucleotides.

Thus, the antisense oligomer sequences of the invention preferably have at least 75%, more preferably at least 85%, more preferably at least 86, 87, 88, 89 or 90% homology to the sequences shown in the sequence listings herein. More preferably there is at least 91, 92, 93 94, or 95%, more preferably at least 96, 97, 98% or 99%, homology. Generally, the shorter the length of the antisense oligomer, the greater the homology required to obtain selective hybridisation. Consequently, where an antisense oligomer of the invention consists of less than about 30 nucleotides, it is preferred that the percentage identity is greater than 75%, preferably greater than 85, 86, 87, 88, 89, 90, 91, 92, 93, 94, 95%, 96, 97, 98% or 99% compared with the antisense oligomers set out in the sequence listings herein. Nucleotide homology comparisons may be conducted by sequence comparison programs such as the GCG Wisconsin Bestfit program or GAP (Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

The antisense oligomer of the present invention may have regions of reduced homology, and regions of exact homology with the target sequence. It is not necessary for an oligomer to have exact homology for its entire length. For example, the oligomer may have continuous stretches of at least 4 or 5 bases that are identical to the target sequence, preferably continuous stretches of at least 6 or 7 bases that are identical to the target sequence, more preferably continuous stretches of at least 8 or 9 bases that are identical to the target sequence. The oligomer may have stretches of at least 10, 11, 12, 13, 14, 15, 16, 17, 18, 19, 20, 21, 22, 23, 24, 25 or 26 bases that are identical to the target sequence. The remaining stretches of oligomer sequence may be intermittently identical with the target sequence; for example, the remaining sequence may have an identical base, followed by a non-identical base, followed by an identical base. Alternatively (or as well) the oligomer sequence may have several stretches of identical sequence (for example 3, 4, 5 or 6 bases) interspersed with stretches of less than perfect homology. Such sequence mismatches will preferably have no or very little loss of splice switching activity.

The term "modulate" or "modulates" includes to "increase" or "decrease" one or more quantifiable parameters, optionally by a defined and/or statistically significant amount. The terms "increase" or "increasing," "enhance" or "enhancing," or "stimulate" or "stimulating" refer generally to the ability of one or antisense oligomers or compositions to produce or cause a greater physiological response (i.e., downstream effects) in a cell or a subject relative to the response caused by either no antisense oligomer or a control compound. The terms "decreasing" or "decrease" refer generally to the ability of one or antisense oligomers or compositions to produce or cause a reduced physiological response (i.e., downstream effects) in a cell or a subject relative to the response caused by either no antisense oligomer or a control compound.

Relevant physiological or cellular responses (in vivo or in vitro) will be apparent to persons skilled in the art, and may include increases in the exclusion of specific exons in a IGTA4-coding pre-mRNA, decreases in the amount of IGTA4-coding pre-mRNA or decreases in the expression of functional IGTA4 protein in a cell, tissue, or subject in need thereof. An "increased" or "enhanced" amount is typically a statistically significant amount, and may include an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1, e.g., 1.5, 1.6, 1.7. 1.8) the amount produced by no antisense oligomer (the absence of an agent) or a control compound. The term "reduce" or "inhibit" may relate generally to the ability of one or more antisense oligomers or compositions to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in the symptoms or pathology of a disease such as MS. A "decrease" in a response may be statistically significant as compared to the response produced by no antisense oligomer or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

The length of an antisense oligomer may vary, as long as it is capable of binding selectively to the intended location within the pre-mRNA molecule. The length of such sequences can be determined in accordance with selection procedures described herein. Generally, the antisense oligomer will be from about 10 nucleotides in length, up to about 50 nucleotides in length. It will be appreciated, however, that any length of nucleotides within this range may be used in the method. Preferably, the length of the antisense oligomer is between 10 and 40, 10 and 35, 15 to 30 nucleotides in length or 20 to 30 nucleotides in length, most preferably about 25 to 30 nucleotides in length. For example, the oligomer may be 20, 21, 22, 23, 24, 25, 26, 27, 28, 29 or 30 nucleotides in length.

As used herein, an "antisense oligomer" refers to a linear sequence of nucleotides, or nucleotide analogs, that allows the nucleobase to hybridize to a target sequence in an RNA by Watson-Crick base pairing, to form an oligonucleotide: RNA heteroduplex within the target sequence. The terms "antisense oligomer", "antisense oligonucleotide", "oligomer" and "antisense compound" may be used interchangeably to refer to an oligonucleotide. The cyclic subunits may be based on ribose or another pentose sugar or, in certain embodiments, a morpholino group (see description of morpholino oligonucleotides below). Also contemplated are peptide nucleic acids (PNAs), locked nucleic acids (LNAs), and 2'-O-Methyl oligonucleotides, among other antisense agents known in the art.

Included are non-naturally-occurring antisense oligomers, or "oligonucleotide analogs", including antisense oligomers or oligonucleotides having (i) a modified backbone structure, e.g., a backbone other than the standard phosphodiester linkage found in naturally-occurring oligo- and polynucleotides, and/or (ii) modified sugar moieties, e.g., morpholino moieties rather than ribose or deoxyribose moieties. Oligonucleotide analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

One method for producing antisense oligomers is the methylation of the 2' hydroxyribose position and the incorporation of a phosphorothioate backbone produces molecules that superficially resemble RNA but that are much more resistant to nuclease degradation, although persons skilled in the art of the invention will be aware of other forms of suitable backbones that may be useable in the objectives of the invention.

To avoid degradation of pre-mRNA during duplex formation with the antisense oligomers, the antisense oligomers used in the method may be adapted to minimise or prevent cleavage by endogenous RNase H. This property is highly preferred, as the treatment of the RNA with the unmethylated oligomers, either intracellular or in crude extracts that contain RNase H, leads to degradation of the pre-mRNA:antisense oligomer duplexes. Any form of modified antisense oligomers that is capable of by-passing or not inducing such degradation may be used in the present method. The nuclease resistance may be achieved by modifying the antisense oligomers of the invention so that it comprises partially unsaturated aliphatic hydrocarbon chain and one or more polar or charged groups including carboxylic acid groups, ester groups, and alcohol groups.

An example of antisense oligomers which when duplexed with RNA are not cleaved by cellular RNase H is 2'-O-methyl derivatives. Such 2'-O-methyl-oligoribonucleotides are stable in a cellular environment and in animal tissues, and their duplexes with RNA have higher Tm values than their ribo- or deoxyribo-counterparts. Alternatively, the nuclease resistant antisense oligomers of the invention may have at least one of the last 3'-terminus nucleotides fluoridated. Still alternatively, the nuclease resistant antisense oligomers of the invention have phosphorothioate bonds linking between at least two of the last 3-terminus nucleotide bases, preferably having phosphorothioate bonds linking between the last four 3'-terminal nucleotide bases.

Increased splice-switching may also be achieved with alternative oligonucleotide chemistry. For example, the antisense oligomer may be chosen from the list comprising: phosphoramidate or phosphorodiamidate morpholino oligomer (PMO); PMO-X; PPMO; peptide nucleic acid (PNA); a locked nucleic acid (LNA) and derivatives including alpha-L-LNA, 2'-amino LNA, 4'-methyl LNA and 4'-O-methyl LNA; ethylene bridged nucleic acids (ENA) and their derivatives; phosphorothioate oligomer; tricyclo-DNA oligomer (tcDNA); tricyclophosphorothioate oligomer; 2'O-Methyl-modified oligomer (2'-OMe); 2'-O-methoxy ethyl (2'-MOE); 2'-fluoro, 2'-fluroarabino (FANA); unlocked nucleic acid (UNA); hexitol nucleic acid (HNA); cyclohexenyl nucleic acid (CeNA); 2'-amino (2'-NH2); 2'-O-ethyleneamine or any combination of the foregoing as mixmers or as gapmers. To further improve the delivery efficacy, the above mentioned modified nucleotides are often conjugated with fatty acids/lipid/cholesterol/amino acids/carbohydrates/polysaccharides/nanoparticles etc. to the sugar or nucleobase moieties. These conjugated nucleotide derivatives can also be used to construct exon skipping antisense oligomers. Antisense oligomer-induced splice modification of the human ITGA4 gene transcripts have generally used either oligoribonucleotides, PNAs, 2OMe or MOE modified bases on a phosphorothioate backbone. Although 2OMeAOs are used for oligo design, due to their efficient uptake in vitro when delivered as cationic lipoplexes, these compounds are susceptible to nuclease degradation and are not considered ideal for in vivo or clinical applications. When alternative chemistries are used to generate the antisense oligomers of the present invention, the uracil (U) of the sequences provided herein may be replaced by a thymine (T).

Included within the antisense oligomers of the present invention are non-naturally-occurring oligomers, or "oligonucleotide analogues," including oligomers having (i) a modified backbone structure, e.g., a backbone other than the standard phosphodiester linkage found in naturally-occurring oligo- and polynucleotides, and/or (ii) modified sugar moieties, e.g., morpholino moieties rather than ribose or deoxyribose moieties. Oligomer analogues support bases capable of hydrogen bonding by Watson-Crick base pairing to standard polynucleotide bases, where the analogue backbone presents the bases in a manner to permit such hydrogen bonding in a sequence-specific fashion between the oligomer analog molecule and bases in a standard polynucleotide (e.g., single-stranded RNA or single-stranded DNA). Preferred analogues are those having a substantially uncharged, phosphorus containing backbone.

Antisense oligomers that do not activate RNase H can be made in accordance with known techniques (see, e.g., U.S. Pat. No. 5,149,797). Such antisense oligomers, which may be deoxyribonucleotide or ribonucleotide sequences, simply contain any structural modification which sterically hinders or prevents binding of RNase H to a duplex molecule containing the oligomer as one member thereof, which structural modification does not substantially hinder or disrupt duplex formation. Because the portions of the oligomer involved in duplex formation are substantially different from those portions involved in RNase H binding thereto, numerous antisense oligomers that do not activate RNase H are available. For example, such antisense oligomers may be oligomers wherein at least one, or all, of the inter-nucleotide bridging phosphate residues are modified phosphates, such as methyl phosphonates, methyl phosphorothioates, phosphoromorpholidates, phosphoropiperazidates boranophosphates, amide linkages and phosphoramidates. For example, every other one of the internucleotide bridging phosphate residues may be modified as described. In another non-limiting example, such antisense oligomers are molecules wherein at least one, or all, of the nucleotides contain a 2' lower alkyl moiety (such as, for example, $C_1$-$C_4$, linear or branched, saturated or unsaturated alkyl, such as methyl, ethyl, ethenyl, propyl, 1-propenyl, 2-propenyl, and isopropyl). For example, every other one of the nucleotides may be modified as described.

While the antisense oligomers described above are a preferred form of the antisense oligomers of the present invention, the present invention includes other oligomeric antisense molecules, including but not limited to oligomer mimetics such as are described below.

Specific examples of preferred antisense oligomers useful in this invention include oligomers containing modified backbones or non-natural inter-nucleoside linkages. As defined in this specification, oligomers having modified backbones include those that retain a phosphorus atom in the backbone and those that do not have a phosphorus atom in the backbone. For the purposes of this specification, and as sometimes referenced in the art, modified oligomers that do not have a phosphorus atom in their inter-nucleoside backbone can also be considered to be antisense oligomers.

In other preferred oligomer mimetics, both the sugar and the inter-nucleoside linkage, i.e., the backbone, of the nucleotide units are replaced with novel groups. The base units are maintained for hybridization with an appropriate nucleic acid target compound. One such oligomeric compound, an oligomer mimetic that has been shown to have excellent hybridization properties, is referred to as a peptide nucleic acid (PNA). In PNA compounds, the sugar-backbone of an oligomer is replaced with an amide containing backbone, in particular an aminoethylglycine backbone. The nucleo-bases are retained and are bound directly or indirectly to aza nitrogen atoms of the amide portion of the backbone.

Another preferred chemistry is the phosphorodiamidate morpholino oligomer (PMO) oligomeric compounds, which are not degraded by any known nuclease or protease. These compounds are uncharged, do not activate RNase H activity when bound to a RNA strand and have been shown to exert sustained splice modulation after in vivo administration (Summerton and Weller, Antisense Nucleic Acid Drug Development, 7, 187-197).

Modified oligomers may also contain one or more substituted sugar moieties. Oligomers may also include nucleobase (often referred to in the art simply as "base") modifications or substitutions. Certain nucleobases are particularly useful for increasing the binding affinity of the oligomeric compounds of the invention. These include 5-substituted pyrimidines, 6-azapyrimidines, and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C., even more particularly when combined with 2'-O-methoxyethyl sugar modifications.

Another modification of the oligomers of the invention involves chemically linking to the oligomer one or more moieties or conjugates that enhance the activity, cellular distribution or cellular uptake of the oligomer. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, myristyl, or an octadecylamine or hexylamino-carbonyl-oxycholesterol moiety.

Cell penetrating peptides have been added to phosphorodiamidate morpholino oligomers to enhance cellular uptake and nuclear localization. Different peptide tags have been shown to influence efficiency of uptake and target tissue specificity, as shown in Jearawiriyapaisam et al. (2008), Mol. Ther. 16 9, 1624-1629.

It is not necessary for all positions in a given compound to be uniformly modified, and in fact more than one of the aforementioned modifications may be incorporated in a single compound or even at a single nucleoside within an oligomer. The present invention also includes antisense oligomers that are chimeric compounds. "Chimeric" antisense oligomers or "chimeras," in the context of this invention, are antisense oligomers, particularly oligomers, which contain two or more chemically distinct regions, each made up of at least one monomer unit, i.e., a nucleotide in the case of an oligomer compound. These oligomers typically contain at least one region wherein the oligomer is modified so as to confer upon the oligomer or antisense oligomer increased resistance to nuclease degradation, increased cellular uptake, and an additional region for increased binding affinity for the target nucleic acid.

The activity of antisense oligomers and variants thereof can be assayed according to routine techniques in the art. For example, splice forms and expression levels of surveyed RNAs and proteins may be assessed by any of a wide variety of well-known methods for detecting splice forms and/or expression of a transcribed nucleic acid or protein. Non-limiting examples of such methods include RT-PCR of spliced forms of RNA followed by size separation of PCR products, nucleic acid hybridization methods e.g., Northern blots and/or use of nucleic acid arrays; nucleic acid amplification methods; immunological methods for detection of proteins; protein purification methods; and protein function or activity assays.

RNA expression levels can be assessed by preparing mRNA/cDNA (i.e., a transcribed polynucleotide) from a cell, tissue or organism, and by hybridizing the mRNA/cDNA with a reference polynucleotide, which is a complement of the assayed nucleic acid, or a fragment thereof. cDNA can, optionally, be amplified using any of a variety of polymerase chain reaction or in vitro transcription methods prior to hybridization with the complementary polynucleotide; preferably, it is not amplified. Expression of one or more transcripts can also be detected using quantitative PCR to assess the level of expression of the transcript(s).

The present invention provides antisense oligomer induced splice-switching of the ITGA4 gene transcript, clinically relevant oligomer chemistries and delivery systems to direct ITGA4 splice manipulation to therapeutic levels. Substantial decreases in the amount of full length ITGA4 mRNA, and hence ITGA4 protein from ITGA4 gene transcription, are achieved by:

1) oligomer refinement in vitro using fibroblast cell lines, through experimental assessment of (i) intronic-enhancer target motifs, (ii) antisense oligomer length and development of oligomer cocktails, (iii) choice of chemistry, and (iv) the addition of cell-penetrating peptides (CPP) to enhance oligomer delivery; and
2) detailed evaluation of a novel approach to generate ITGA4 transcripts with one or more missing exons.

As such, it is demonstrated herein that processing of ITGA4 pre-mRNA can be manipulated with specific antisense oligomers. In this way functionally significant decreases in the amount of ITGA4 protein can be obtained, thereby reducing the severe pathology associated with MS.

The antisense oligomers used in accordance with this invention may be conveniently made through the well-known technique of solid phase synthesis. Equipment for such synthesis is sold by several vendors including, for example, Applied Biosystems (Foster City, Calif.). One method for synthesising oligomers on a modified solid support is described in U.S. Pat. No. 4,458,066.

Any other means for such synthesis known in the art may additionally or alternatively be employed. It is well known to use similar techniques to prepare oligomers such as the phosphorothioates and alkylated derivatives. In one such automated embodiment, diethyl-phosphoramidites are used as starting materials and may be synthesized as described by Beaucage, et al., (1981) Tetrahedron Letters, 22:1859-1862.

The antisense oligomers of the invention are synthesised in vitro and do not include antisense compositions of biological origin, or genetic vector constructs designed to direct the in vivo synthesis of antisense oligomers. The molecules of the invention may also be mixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption.

The antisense oligomers of the present invention also can be used as a prophylactic or therapeutic, which may be utilised for the purpose of treatment of a disease. Accordingly, in one embodiment the present invention provides antisense oligomers that bind to a selected target in the ITGA4 pre-mRNA to induce efficient and consistent exon skipping as described herein, in a therapeutically effective amount, admixed with a pharmaceutically acceptable carrier, diluent, or excipient.

The invention therefore provides a pharmaceutical, prophylactic, or therapeutic composition to treat, prevent or ameliorate the effects of a disease associated with ITGA4 expression in a patient, the composition comprising:
  a) one or more antisense oligomers as described herein, and
  b) one or more pharmaceutically acceptable carriers and/or diluents.

Preferably the disease associated with ITGA4 expression is MS.

The composition may comprise about 1 nM to 1000 nM of each of the desired antisense oligomer(s) of the invention. Preferably, the composition may comprise about 1 nM to 500 nM, 10 nM to 500 nM, 50 nM to 750 nM, 10 nM to 500 nM, 1 nM to 100 nM, 1 nM to 50 nM, 1 nM to 40 nM, 1 nM to 30 nM, 1 nM to 20 nM, most preferably between 1 nM and 10 nM of each of the antisense oligomer(s) of the invention.

The composition may comprise about 1 nm, 2 nm, 3 nm, 4 nm, 5 nm, 6 nm, 7 nm, 8 nm, 9 nm, 10 nm, 20 nm, 50 nm, 75 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm or 1000 nm of each of the desired antisense oligomer(s) of the invention.

The present invention further provides one or more antisense oligomers adapted to aid in the prophylactic or therapeutic treatment, prevention or amelioration of symptoms of a disease such as an ITGA4 expression related disease or pathology in a form suitable for delivery to a patient.

The phrase "pharmaceutically acceptable" refers to molecular entities and compositions that are physiologically tolerable and do not typically produce an allergic or similarly untoward reaction, such as gastric upset and the like, when administered to a patient. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in Martin, *Remington's Pharmaceutical Sciences*, 18th Ed., Mack Publishing Co., Easton, Pa., (1990).

In a more specific form of the invention there are provided pharmaceutical compositions comprising therapeutically effective amounts of one or more antisense oligomers of the invention together with pharmaceutically acceptable diluents, preservatives, solubilizers, emulsifiers, adjuvants, and/or carriers. Such compositions include diluents of various buffer content (e.g. Tris-HCl, acetate, phosphate), pH and ionic strength and additives such as detergents and solubilizing agents (e.g. Tween 80, Polysorbate 80), antioxidants (e.g., ascorbic acid, sodium metabisulfite), preservatives (e.g. Thimersol, benzyl alcohol) and bulking substances (e.g., lactose, mannitol). The material may be incorporated into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, for example, Martin, *Remington's Pharmaceutical Sciences*, 18th Ed. (1990, Mack Publishing Co., Easton, Pa. 18042) pages 1435-1712 that are herein incorporated by reference. The compositions may be prepared in liquid form, or may be in dried powder, such as a lyophilised form.

It will be appreciated that pharmaceutical compositions provided according to the present invention may be administered by any means known in the art. Preferably, the pharmaceutical compositions for administration are administered by injection, orally, topically or by the pulmonary or nasal route. The antisense oligomers are more preferably delivered by intravenous, intra-arterial, intraperitoneal, intramuscular or subcutaneous routes of administration. The appropriate route may be determined by one of skill in the art, as appropriate to the condition of the subject under treatment. Vascular or extravascular circulation, the blood or lymph system, and the cerebrospinal fluid are some non-limiting sites where the antisense oligomer may be introduced. Direct CNS delivery may be employed, for instance, intracerebral ventribular or intrathecal administration may be used as routes of administration.

Formulations for topical administration include those in which the oligomers of the disclosure are in admixture with a topical delivery agent such as lipids, liposomes, fatty acids, fatty acid esters, steroids, chelating agents and surfactants. Lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). For topical or other administration, oligomers of the disclosure may be encapsulated within liposomes or may form complexes thereto, in particular to cationic liposomes. Alternatively, oligomers may be complexed to lipids, in particular to cationic lipids. Fatty acids and esters, pharmaceutically acceptable salts thereof, and their uses are further described in U.S. Pat. No. 6,287,860 and/or U.S. patent application Ser. No. 09/315,298 filed on May 20, 1999.

In certain embodiments, the antisense oligomers of the disclosure can be delivered by transdermal methods (e.g., via incorporation of the antisense oligomers into, e.g., emulsions, with such antisense oligomers optionally packaged into liposomes). Such transdermal and emulsion/liposome-mediated methods of delivery are described for delivery of antisense oligomers in the art, e.g., in U.S. Pat. No. 6,965,025.

The antisense oligomers described herein may also be delivered via an implantable device. Design of such a device is an art-recognized process, with, e.g., synthetic implant design described in, e.g., U.S. Pat. No. 6,969,400.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Oral formulations are those in which oligomers of the disclosure are administered in conjunction with one or more penetration enhancers surfactants and chelators. Surfactants include fatty acids and/or esters or salts thereof, bile acids and/or salts thereof. Bile acids/salts and fatty acids and their uses are further described in U.S. Pat. No. 6,287,860. In some embodiments, the present disclosure provides combinations of penetration enhancers, for example, fatty acids/salts in combination with bile acids/salts. An exemplary combination is the sodium salt of lauric acid, capric acid and UDCA. Further penetration enhancers include polyoxyethylene-9-lauryl ether, polyoxyethylene-20-cetyl ether. Oligomers of the disclosure may be delivered orally, in granular form including sprayed dried particles, or complexed to form micro or nanoparticles. Oligomer complexing agents and their uses are further described in U.S. Pat. No. 6,287,860. Oral formulations for oligomers and their preparation are described in detail in U.S. Pat. No. 6,887,906, 09/315,298 filed May 20, 1999 and/or US20030027780.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

The delivery of a therapeutically useful amount of antisense oligomers may be achieved by methods previously published. For example, intracellular delivery of the antisense oligomer may be via a composition comprising an admixture of the antisense oligomer and an effective amount of a block copolymer. An example of this method is described in US patent application US20040248833. Other methods of delivery of antisense oligomers to the nucleus are described in Mann C J et al. (2001) Proc, Natl. Acad. Science, 98(1) 42-47, and in Gebski et al. (2003) Human Molecular Genetics, 12(15): 1801-1811. A method for introducing a nucleic acid molecule into a cell by way of an expression vector either as naked DNA or complexed to lipid carriers, is described in U.S. Pat. No. 6,806,084.

In certain embodiments, the antisense oligomers of the invention and therapeutic compositions comprising the same can be delivered by transdermal methods (e.g., via incorporation of the antisense oligomers into, e.g., emulsions, with such antisense oligomers optionally packaged into liposomes). Such transdermal and emulsion/liposome-mediated methods of delivery are described for delivery of antisense oligomers in the art, e.g., in U.S. Pat. No. 6,965,025.

It may be desirable to deliver the antisense oligomer in a colloidal dispersion system. Colloidal dispersion systems include macromolecule complexes, nanocapsules, microspheres, beads, and lipid-based systems including oil-in-water emulsions, micelles, mixed micelles, and liposomes or liposome formulations. These colloidal dispersion systems can be used in the manufacture of therapeutic pharmaceutical compositions.

Liposomes are artificial membrane vesicles, which are useful as delivery vehicles in vitro and in vivo. These formulations may have net cationic, anionic, or neutral charge characteristics and have useful characteristics for in vitro, in vivo and ex vivo delivery methods. It has been shown that large unilamellar vesicles can encapsulate a substantial percentage of an aqueous buffer containing large macromolecules. RNA and DNA can be encapsulated within the aqueous interior and be delivered to cells in a biologically active form (Fraley, et al., Trends Biochem. Sci. 6:77, 1981).

In order for a liposome to be an efficient gene transfer vehicle, the following characteristics should be present: (1) encapsulation of the antisense oligomer of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988). The composition of the liposome is usually a combination of phospholipids, particularly high phase-transition-temperature phospholipids, usually in combination with steroids, especially cholesterol. Other phospholipids or other lipids may also be used. The physical characteristics of liposomes depend on pH, ionic strength, and the presence of divalent cations. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The antisense oligomers described herein may also be delivered via an implantable device. Design of such a device is an art-recognized process, with, e.g., synthetic implant design described in, e.g., U.S. Pat. No. 6,969,400, the contents of which are incorporated in their entirety by reference herein.

Antisense oligomers can be introduced into cells using art-recognized techniques (e.g., transfection, electroporation, fusion, liposomes, colloidal polymeric particles and viral and non-viral vectors as well as other means known in the art). The method of delivery selected will depend at least on the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

As known in the art, antisense oligomers may be delivered using, for example, methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49, incorporated by reference in its entirety).

The antisense oligomer may also be combined with other pharmaceutically acceptable carriers or diluents to produce a pharmaceutical composition. Suitable carriers and diluents include isotonic saline solutions, for example phosphate-buffered saline. The composition may be formulated for parenteral, intramuscular, intravenous, subcutaneous, intraocular, oral, or transdermal administration.

The routes of administration described are intended only as a guide since a skilled practitioner will be able to readily determine the optimum route of administration and any dosage for any particular animal and condition.

Multiple approaches for introducing functional new genetic material into cells, both in vitro and in vivo have been attempted (Friedmann (1989) Science, 244:1275-1280). These approaches include integration of the gene to be expressed into modified retroviruses (Friedmann (1989) supra; Rosenberg (1991) Cancer Research 51(18), suppl.: 5074S-5079S); integration into non-retrovirus vectors (Rosenfeld, et al. (1992) Cell, 68:143-155; Rosenfeld, et al. (1991) Science, 252:431-434); or delivery of a transgene linked to a heterologous promoter-enhancer element via liposomes (Friedmann (1989), supra; Brigham, et al. (1989) Am. J. Med. Sci., 298:278-281; Nabel, et al. (1990) Science, 249:1285-1288; Hazinski, et al. (1991) Am. J. Resp. Cell Molec. Biol., 4:206-209; and Wang and Huang (1987) Proc. Natl. Acad. Sci. (USA), 84:7851-7855); coupled to ligand-specific, cation-based transport systems (Wu and Wu (1988) J. Biol. Chem., 263:14621-14624) or the use of naked DNA, expression vectors (Nabel et al. (1990), supra); Wolff et al. (1990) Science, 247:1465-1468). Direct injection of transgenes into tissue produces only localized expression (Rosenfeld (1992) supra); Rosenfeld et al. (1991) supra; Brigham et al. (1989) supra; Nabel (1990) supra; and Hazinski et al. (1991) supra). The Brigham et al. group (Am. J. Med. Sci. (1989) 298:278-281 and Clinical Research (1991) 39 (abstract)) have reported in vivo transfection only of lungs of mice following either intravenous or intratracheal administration of a DNA liposome complex. An example of a review article of human gene therapy procedures is: Anderson, Science (1992) 256:808-813; Barteau et al. (2008), Curr Gene Ther; 8(5):313-23; Mueller et al. (2008). Clin Rev Allergy Immunol; 35(3):164-78; Li et al. (2006) Gene Ther., 13(18):1313-9; Simoes et al. (2005) Expert Opin Drug Deliv; 2(2):237-54.

The antisense oligomers of the invention encompass any pharmaceutically acceptable salts, esters, or salts of such esters, or any other compound which, upon administration to an animal including a human, is capable of providing (directly or indirectly) the biologically active metabolite or residue thereof. Accordingly, as an example, the disclosure is also drawn to prodrugs and pharmaceutically acceptable salts of the compounds of the invention, pharmaceutically acceptable salts of such pro-drugs, and other bioequivalents.

The term "pharmaceutically acceptable salts" refers to physiologically and pharmaceutically acceptable salts of the compounds of the invention: i.e. salts that retain the desired biological activity of the parent compound and do not impart undesired toxicological effects thereto. For oligomers, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. The pharmaceutical compositions of the present invention may be administered in a number of ways depending upon whether local or systemic treatment is desired and upon the area to be treated. Administration may be topical (including ophthalmic and mucous membranes, as well as rectal delivery), pulmonary, e.g., by inhalation or insufflation of powders or aerosols (including by nebulizer, intratracheal, intranasal, epidermal and transdermal), oral or parenteral. Parenteral administration includes intravenous, intra-arterial, subcutaneous, intraperitoneal or intramuscular injection or infusion; or intracranial, e.g., intrathecal or intraventricular, administration. Oligomers with at least one 2'-O-methoxyethyl modification are believed to be particularly useful for oral administration. Preferably, the antisense oligomer is delivered via the subcutaneous or intravenous route.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

In one embodiment, the antisense oligomer is administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1 mg to 1000 mg oligomer per 70 kg. In some cases, doses of greater than 1000 mg oligomer/patient may be necessary. For i.v. administration, preferred doses are from about 0.5 mg to 1000 mg oligomer per 70 kg. For intra venous or sub cutaneous administration, the antisense oligomer may be administered at a dosage of about 120 mg/kg daily or weekly.

The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on EC50s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligomer is administered in maintenance doses, ranging from 0.01 µg to 100 g per kg of body weight, once or more daily, to once every 20 years.

An effective in vivo treatment regimen using the antisense oligomers of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of disorder under treatment, and corresponding adjustments in the dose or treatment regimen, in order to achieve an optimal therapeutic outcome.

Treatment may be monitored, e.g., by general indicators of disease known in the art. The efficacy of an in vivo administered antisense oligomers of the invention may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of a mutant mRNA in relation to a reference normal mRNA or protein as determined by standard techniques such as RT-PCR, Northern blotting, ELISA or Western blotting.

Intranuclear oligomer delivery is a major challenge for antisense oligomers. Different cell-penetrating peptides (CPP) localize PMOs to varying degrees in different conditions and cell lines, and novel CPPs have been evaluated by the inventors for their ability to deliver PMOs to the target cells. The terms CPP or "a peptide moiety which enhances cellular uptake" are used interchangeably and refer to cationic cell penetrating peptides, also called "transport peptides", "carrier peptides", or "peptide transduction domains". The peptides, as shown herein, have the capability of inducing cell penetration within about or at least about 30%, 40%, 50%, 60%, 70%, 80%, 90%, or 100% of cells of a given cell culture population and allow macromolecular translocation within multiple tissues in vivo upon systemic administration. CPPs are well-known in the art and are disclosed, for example in U.S. Application No. 2010/0016215, which is incorporated by reference in its entirety.

The present invention therefore provides antisense oligomers of the present invention win combination with cell-penetrating peptides for manufacturing therapeutic pharmaceutical compositions.

According to a still further aspect of the invention, there is provided one or more antisense oligomers as described herein for use in an antisense oligomer-based therapy. Preferably, the therapy is for a condition related to ITGA4 expression. More preferably, the therapy for a condition related to ITGA4 expression is therapy for MS.

More specifically, the antisense oligomer may be selected from the group consisting of any one or more of SEQ ID NOs: 1-202, and combinations or cocktails thereof. This includes sequences which can hybridise to such sequences under stringent hybridisation conditions, sequences complementary thereto, sequences containing modified bases, modified backbones, and functional truncations or extensions thereof which possess or modulate pre-mRNA processing activity in an ITGA4 gene transcript.

The invention extends also to a combination of two or more antisense oligomers capable of binding to a selected target to induce exon exclusion in an ITGA4 gene transcript. The combination may be a cocktail of two or more antisense oligomers, a construct comprising two or more or two or more antisense oligomers joined together for use in an antisense oligomer-based therapy.

The invention provides a method to treat, prevent or ameliorate the effects of a disease associated with ITGA4 expression, comprising the step of:
a) administering to the patient an effective amount of one or more antisense oligomers or pharmaceutical composition comprising one or more antisense oligomers as described herein.

Furthermore, the invention provides a method to treat, prevent or ameliorate the effects of multiple sclerosis, comprising the step of:
a) administering to the patient an effective amount of one or more antisense oligomers or pharmaceutical composition comprising one or more antisense oligomers as described herein.

Preferably, the therapy is used to reduce the levels of functional IGTA4 protein via an exon skipping strategy. The reduction in levels of ITGA4 is preferably achieved by reducing the transcripts level through modifying pre-mRNA splicing in the integrin alpha-4 (ITGA4) gene transcript or part thereof.

The reduction in ITGA4 will preferably lead to a reduction in the quantity, duration or severity of the symptoms of an ITGA4-related condition or pathology, such as MS.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

According to another aspect of the invention there is provided the use of one or more antisense oligomers as described herein in the manufacture of a medicament for the modulation or control of a disease associated with ITGA4 expression.

The invention also provides for the use of purified and isolated antisense oligomers as described herein, for the manufacture of a medicament for treatment of a disease associated with ITGA4 expression.

There is provided the use of purified and isolated antisense oligomers as described herein for the manufacture of a medicament to treat, prevent or ameliorate the effects of a disease associated with ITGA4 expression.

Preferably, the ITGA4-related pathology or disease is MS.

The invention extends, according to a still further aspect thereof, to cDNA or cloned copies of the antisense oligomer sequences of the invention, as well as to vectors containing the antisense oligomer sequences of the invention. The invention extends further also to cells containing such sequences and/or vectors.

The invention also provides kits to treat, prevent or ameliorate a disease or condition associated with ITGA4 expression in a patient, which kit comprises at least an isolated or purified antisense oligomer for modifying pre-mRNA splicing in an ITGA4 gene transcript or part thereof, packaged in a suitable container, together with instructions for its use.

In a preferred embodiment, the kits will contain at least one antisense oligomer as described herein or as shown in Tables 3 to 7, or a cocktail of antisense oligomers, as described herein. The kits may also contain peripheral reagents such as buffers, stabilizers, etc.

There is therefore provided a kit to treat, prevent or ameliorate a disease or condition associated with ITGA4 expression in a patient, which kit comprises at least an antisense oligomer described herein or as shown in Tables 3 to 7 and combinations or cocktails thereof, packaged in a suitable container, together with instructions for its Use.

There is also provided a kit to treat, prevent or ameliorate a disease or condition associated with ITGA4 expression in a patient which kit comprises at least an antisense oligomer selected from the group consisting of any one or more of SEQ ID NOs: 1-202, and combinations or cocktails thereof, packaged in a suitable container, together with instructions for its use.

Preferably, the disease or condition is multiple sclerosis.

The contents of the kit can be lyophilized and the kit can additionally contain a suitable solvent for reconstitution of the lyophilized components. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale for human administration.

When the components of the kit are provided in one or more liquid solutions, the liquid solution can be an aqueous solution, for example a sterile aqueous solution. For in vivo use, the expression construct may be formulated into a pharmaceutically acceptable syringeable composition. In this case the container means may itself be an inhalant, syringe, pipette, eye dropper, or other such like apparatus, from which the formulation may be applied to an affected area of the animal, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle.

Those of ordinary skill in the field should appreciate that applications of the above method has wide application for identifying antisense oligomers suitable for use in the treatment of many other diseases.

The antisense oligomers of the present invention may also be used in conjunction with alternative therapies, such as drug therapies.

The present invention therefore provides a method of treating, preventing or ameliorating the effects of a disease or condition associated with ITGA4 expression, wherein the antisense oligomers of the present invention and administered sequentially or concurrently with another alternative therapy associated with treating, preventing or ameliorating the effects of a disease or condition associated with ITGA4 expression. Preferably, the disease or condition is MS.

The alternative therapy may be chosen from the list comprising interferon beta-1a, interferon beta-1b, glatiramer acetate, mitoxantrone, natalizumab, fingolimod, teriflunomide, dimethyl fumarate and alemtuzumab.

General

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

As used herein the term "derived" and "derived from" shall be taken to indicate that a specific integer may be obtained from a particular source albeit not necessarily directly from that source.

As used herein, the singular forms "a," "an" and "the" include plural references unless the context clearly dictates otherwise.

Throughout this specification, unless the context requires otherwise, the word "comprise", or variations such as "comprises" or "comprising", will be understood to imply the inclusion of a stated integer or group of integers but not the exclusion of any other integer or group of integers.

Other than in the operating example, or where otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the specification and claims are approximations that may vary depending upon the desired properties sought to be obtained by the present invention. Hence "about 80%" means "about 80%" and also "80%". At the very least, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value; however, inherently contains certain errors necessarily resulting from the standard deviation found in their respective testing measurements Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Sequence identity numbers ("SEQ ID NO:") containing nucleotide and amino acid sequence information included in this specification are collected at the end of the description and have been prepared using the program Patentin Version 3.0. Each nucleotide or amino acid sequence is identified in the sequence listing by the numeric indicator <210> followed by the sequence identifier (e.g. <210>1, <210>2, etc.). The length, type of sequence and source organism for each nucleotide or amino acid sequence are indicated by information provided in the numeric indicator fields <211>, <212> and <213>, respectively. Nucleotide and amino acid sequences referred to in the specification are defined by the information provided in numeric indicator field <400> followed by the sequence identifier (e.g. <400>1, <400>2, etc.).

An antisense oligomer nomenclature system was proposed and published to distinguish between the different antisense oligomers (see Mann et al., (2002) J Gen Med 4, 644-654). This nomenclature became especially relevant when testing several slightly different antisense oligomers, all directed at the same target region, as shown below:

H # A/D (x:y)
the first letter designates the species (e.g. H: human, M: murine)
"#" designates target exon number
"A/D" indicates acceptor or donor splice site at the beginning and end of the exon, respectively
(x y) represents the annealing coordinates where "−" or "+" indicate intronic or exonic sequences respectively. As an example, A(−6+18) would indicate the last 6 bases of the intron preceding the target exon and the first 18 bases of the target exon. The closest splice site would be the acceptor so these coordinates would be preceded with an "A". Describing annealing coordinates at the donor splice site could be D(+2-18) where the last 2 exonic bases and the first 18 intronic bases correspond to the annealing site of the antisense oligomer. Entirely exonic annealing coordinates that would be represented by A(+65+85), that is the site between the 65th and 85th nucleotide, inclusive, from the start of that exon.

The following examples serve to more fully describe the manner of using the above-described invention, as well as to set forth the best modes contemplated for carrying out various aspects of the invention. It is understood that these methods in no way serve to limit the true scope of this invention, but rather are presented for illustrative purposes.

EXAMPLES

Example 1

Oligomer Nomenclature

The nomenclature system defines species, exon number, acceptor or donor targeting and annealing coordinates, where "−" indicates intronic position and "+" specifies exonic location from the splice site, as described herein. Some detailed oligomer annealing coordinates are shown in Tables 3 to 7.

Antisense Oligomers

Antisense oligomers with 2-O'Me modification were either synthesized in-house or ordered from Tri Link Bio-Technologies, Inc [San Diego, Calif., USA].

Cell Propagation and Transfection

Primary normal dermal fibroblasts were propagated using well established techniques [Villegas and McPhaul, Curr Protoc Mol Biol (2005) 28.3.1-28.3.9]. Cells were seeded and propagated in 75 $cm^2$ tissue culture flasks and transfection with 2OMeAO was performed in 24 well plates. One day before transfection, 15-17,000 cells were seeded in 24 well plates and transfected with a range of concentrations (5-100 nM) of 2OMeAO using Lipofectin® transfection reagent [Life Technologies: Carlsbad, Calif., USA] (Lipofectin:oligo ratio of 2:1) according to the manufacturer protocol.

For PMO transfection, PMO were annealed to oligonucleotides with reverse complement sequences and the resulting duplex was allowed to form complexes with Lipofectin® (Lipofectin:oligo ratio of 2:1).

Transfected cells were typically incubated for 24 hours, unless otherwise indicated, before RNA was extracted for analysis using TRIzol® acid phenol extraction [Life Technologies: Carlsbad, Calif., USA]. RNA samples were treated with RNase free DNAse 1, although minor DNA contamination is not problematic.

RT-PCR Analysis

One step RT-PCR using Superscript® III [Life Technologies: Carlsbad, Calif., USA]: ~100 ng of total RNA was used as a template and incubated for 30 min at 55° C., and at 94° C. for 2 min, before 30 rounds of 94° C. for 30 sec, 55° C. for 30 sec and 68° C. for 1 min 30 sec using exon 1F and 10R primers for exon 2-9 skipping, exon 9F and 20R primers for exon 10-19 skipping and exon 10F and 28R primers for exon 20-27 skipping.

PCR products were fractionated on 2% agarose gels in Tris-Acetate-EDTA buffer and the images captured on gel documentation system and analysed with Bio1D software [Vilber Lourmat, Eberhardzell, Germany] to quantitate band weight and estimate ratios of full length ITGA4 and exon skipped products. Product identity was confirmed by band purification and DNA sequencing as necessary. The efficiency of exon skipping was determined by calculating the percentage of the transcripts with exon(s) skipped compared to the total product generated by RT-PCR.

Among the antisense oligomers tested, the antisense oligomers targeting exon 3, 4 and 19 produced 30-40% of transcripts with the targeted exon being skipped (Table 3). Based on the size of the transcripts, antisense oligomers targeting exon 3 have induced skipping of both exon 3 and 4, leaving the reading frame intact.

Western Blotting

Proteins were extracted from treated cultures after two days and prepared according to Cooper et al., [Neurology (2003) 61, 93-96], but with 15% SDS. SDS-PAGE electrophoresis was performed using NuPAGE® Novex® 4-12% BIS/Tris gels [Life Technologies: Carlsbad, Calif., USA] run at 200V for 55 mins. Proteins were transferred to Pall Fluorotrans® W PVDF membranes [Pall Corporation, USA] at 290 mA for overnight at 18° C. ITGA4 antibody [Cell Signaling Technology, Inc., USA Cat. No. 4600], which recognizes residues surrounding Ser1027 encoded by exon18, was applied at 1:1000 dilution overnight at 4° C. and β-tubulin was detected by a rabbit polyclonal antibody (1:3000 dilution) overnight at 4° C. (Thermo Scientific Pierce Antibody Products, Rockford Ill. USA Cat. No. PIEPA1-41331), as a reference loading protein, with loadings normalized to the β-tubulin.

For immunodetection, polyclonal goat anti-rabbit immunoglobulins/HRP (Dako®, Cat. no P0448) at a dilution of 1:10,000 and Luminata™ Crescendo Western HRP substrate (Merck Millipore®, Cat. No. WBLUR0100) were used. Quantification was performed using Bio-1 D software [Vilber Lourmat, Eberhardzell, Germany] for image analysis.

Figure 2:
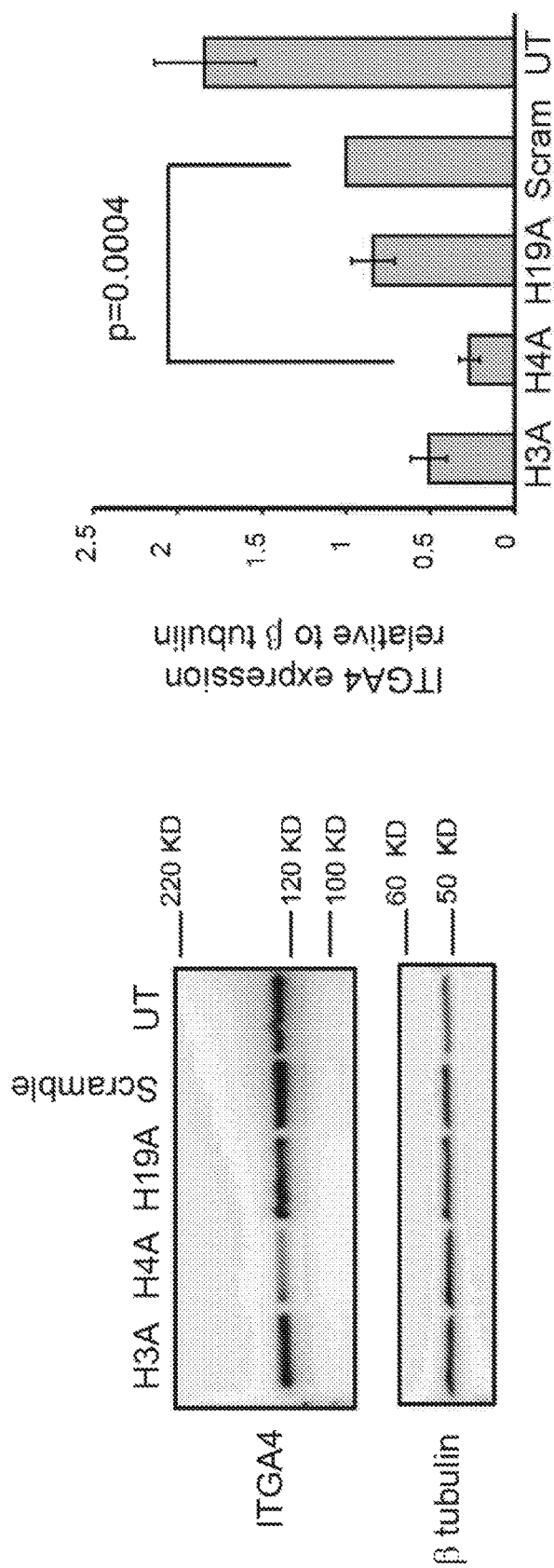
FIG. 2 shows Western blotting data and a graph indicating a knockdown of the ITGA4 protein in normal fibroblasts following treatment with exon skipping antisense oligomers targeting exons 3 (H3A), 4 (H4A) and 19 (H19A) and an oligomer of scrambled sequence. Antisense oligomers were tested at 100 nM. Levels of ITGA4 expression are normalised against β-tubulin expression.

Results are provided in FIG. 2. The results indicate a knockdown of the ITGA4 protein in normal fibroblasts following treatment with exon skipping antisense oligomers targeting exon 3 (AO1), 4 (AO21), and 19 (AO47).

Cell Adhesion Assay 96-well microplates were coated with fibronectin 3 μg/well in PBS (Millipore® Cat. No. FC010), laminin 0.75 μg/well in PBS (Millipore® Cat. No. AG56P) or recombinant human VCAM-1 0.5 ug/well in PBS (R&D Systems™, Cat. No. ADP5-050). Cells were washed twice in PBS and labelled with 2 μM calcein AM fluorescent dye (Invitrogen®, Cat. No. C1430) for 30 min in serum free Dulbecco's modified Eagle's medium (DMEM). After two washes with DMEM, the cells were resuspended in serum free DMEM and plated (30,000 cells/well) and incubated at 37° C. for 30-45 min. The microplate was washed four times with PBS to remove non-adherent cells, and the remaining adherent cells were measured using a fluorescence plate reader, Beckman Coulter DTX-880 Multimode Detector (NSW, Australia) with excitation wavelength of 488 nm and emission detected at 512 nm. In order to calculate the percentage of adherent cells, the fluorescent signals of total cells were analysed in a separate microplate, omitting the wash steps. Background signals were subtracted from all samples and results were normalised to the sample treated with scrambled oligomers which serves as an experimental control. The experiment was independently repeated three times and a Student's t test was performed to determine the p value.

Figure 3:
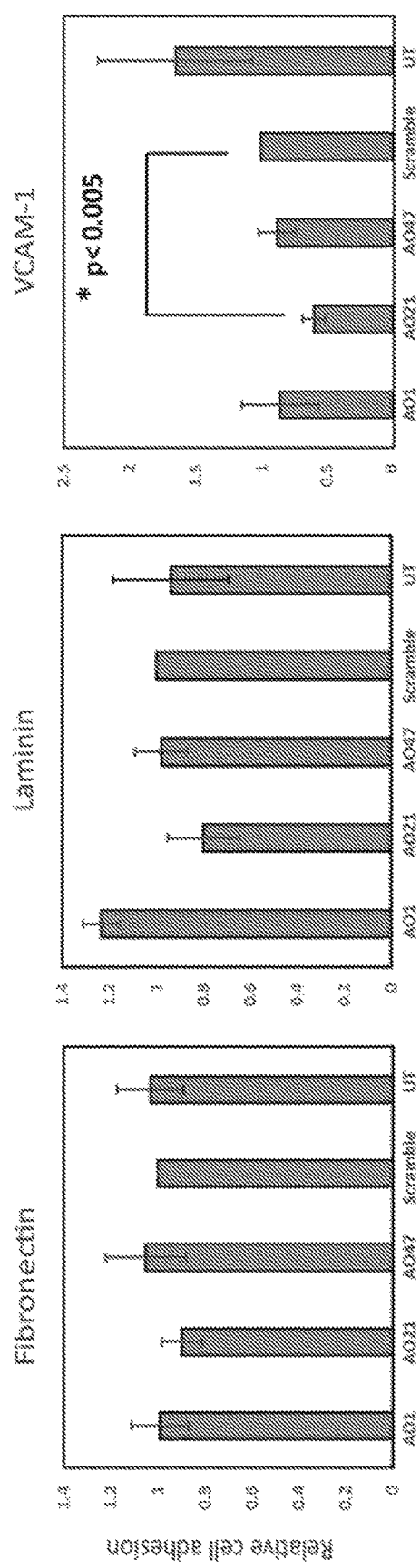
FIG. 3 provides graphs showing the effect of treatment with exon skipping antisense oligomers targeting exons 3 (AO1), 4 (AO21) and 19 (AO47) and an oligomer of scrambled sequence (at 100 nM) on cell adhesion property in normal fibroblasts. The results were an average of three experiments performed independently and data were normalised to the sample treated with scrambled oligomer. The error bars represent standard error mean (SEM). Reduced cell adhesion to the microplate pre-coated with VCAM-1 was observed for the cells pre-treated with antisense oligomers directed to exon 4 (AO21). $p<0.005$ compared to the scrambled oligomer treated samples.
Figures 5A, 5B:
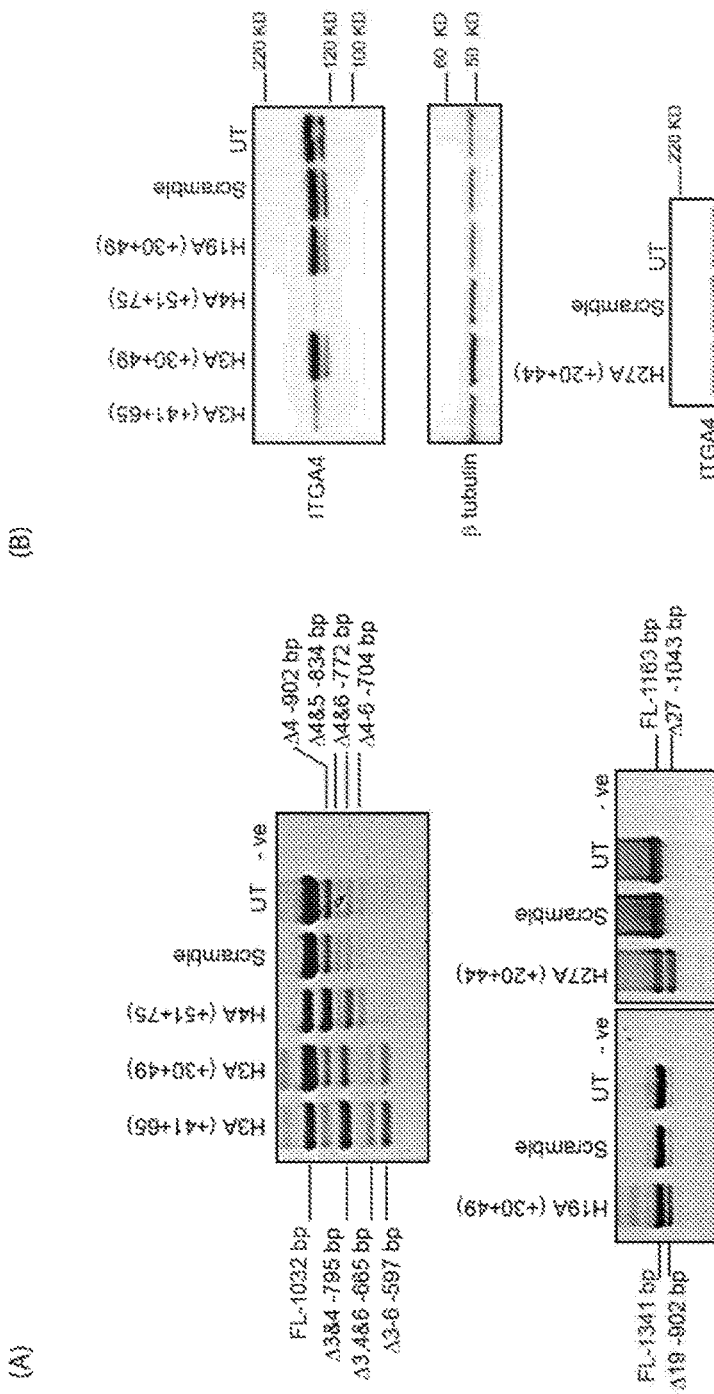
FIG. 5A-C show ITGA4 expression in jurkat cells after nucelofection with different PMOs [H3A (+41+65), H3A (+30+49), H4A (+51+75), H19A (+30+49) and H27A (+20+44)] and scrambled PMO (Scramble) at 500 nM for 3 days.
Figure 5C:
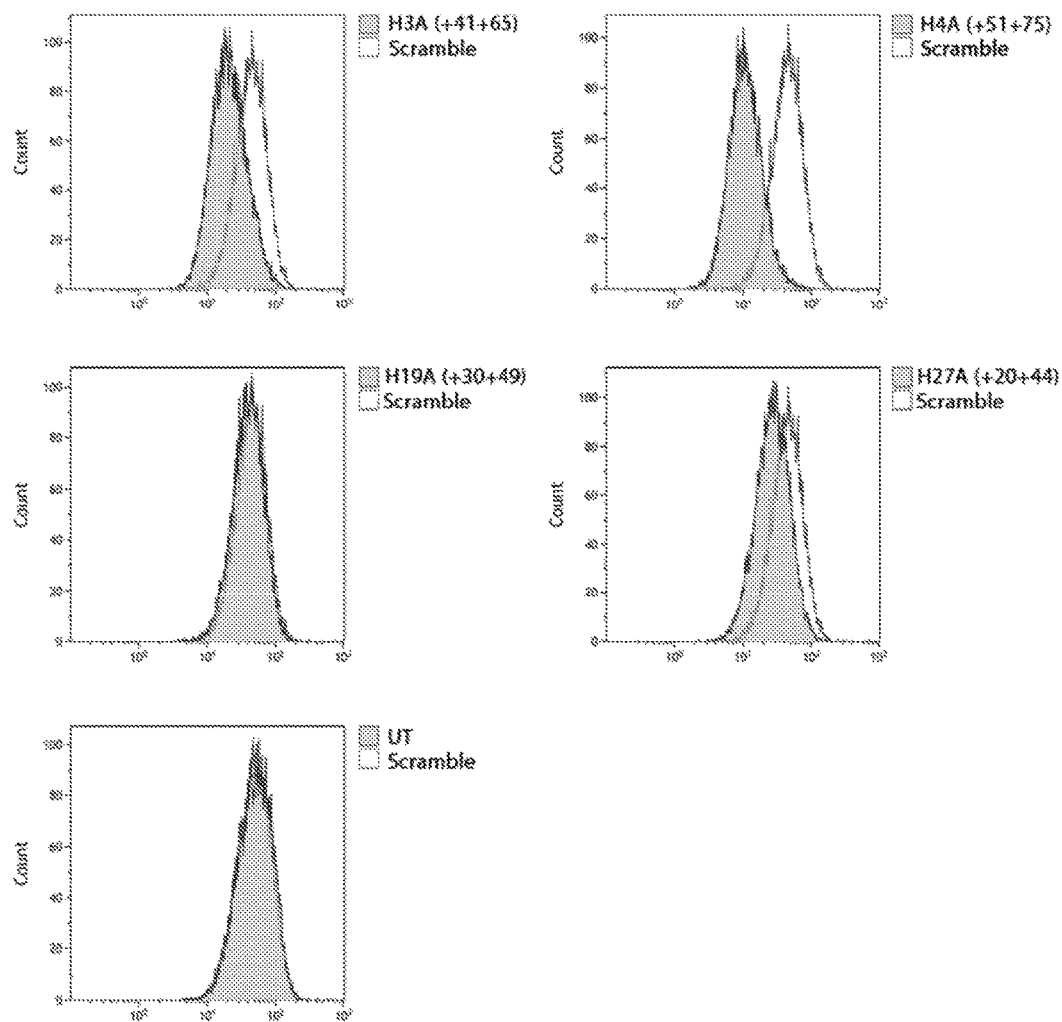
Figure 6A:
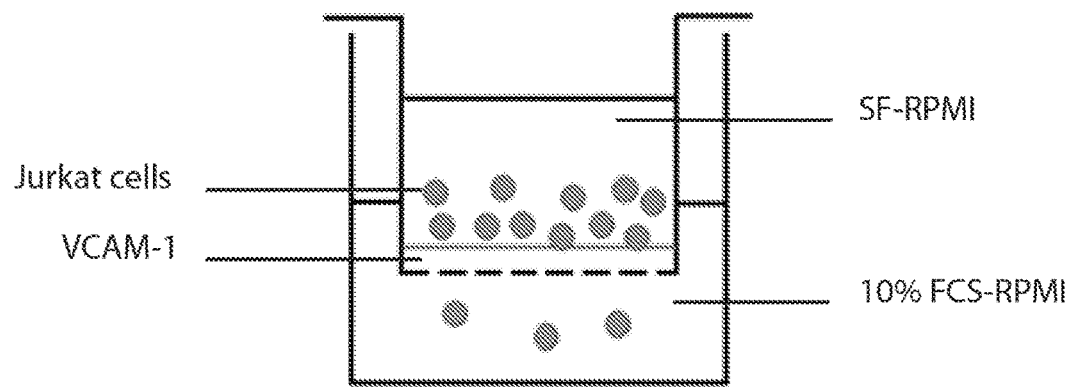
FIG. 6A is a diagram of the setup of the migration test.
Figure 6B:
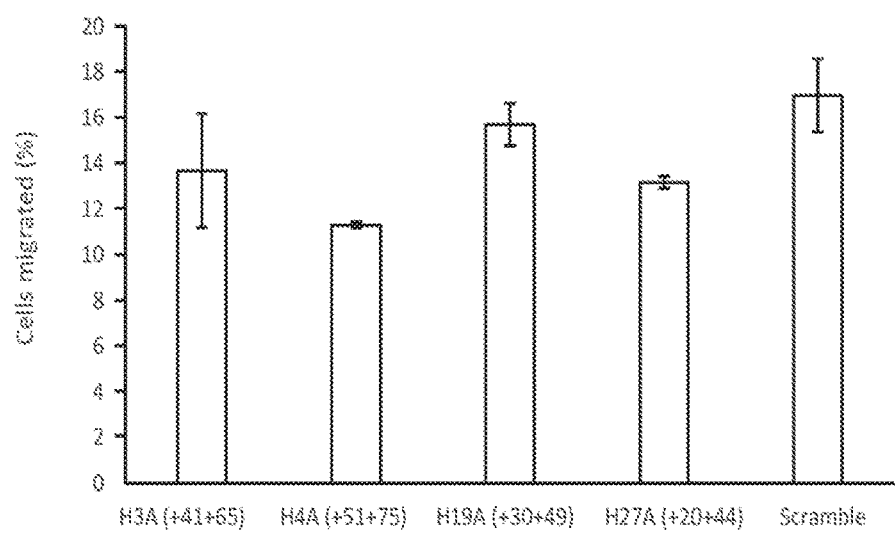
FIG. 6B is a graph of the migration of jurkat cells treated with different PMOs [H3A (+41+65), H4A (+51+75), H19A (+30+49) and H27A (+20+44)] and scrambled PMO (Scramble) at 500 nM for 2 days. The top panel shows the experimental set up for the migration assay and the jurkat cells nucleofected with PMO were allowed to migrate for 5 h. The assay was performed in duplicates. Jurkat cells treated with PMO H4A (+51+75) and H27A (+20+44) show slower migration to the bottom chamber compared to the scrambled treated cells.

As shown in FIG. 3, transfection with oligomers targeting exon 4 (AO21) resulted in a reduction in cells adhering to a microplate pre-coated with VCAM-1. This result correlates with a Western analysis for protein expression which shows that the most reduction in ITGA4 protein expression was observed after treatment with AO21. However, no changes in cell adhesion were observed when these cells were allowed to attach to the plates pre-coated with either fibronectin or laminin. These results indicate that lowering ITGA4 expression has no effect on cellular interaction with fibronectin and laminin. These results are as expected since ITGA4 is not required for interaction with laminin, and several other integrin receptors apart from ITGA4 can interact with fibronectin. On the other hand, ITGA4 is a major integrin receptor for interaction with VCAM-1 and lowering ITGA4 expression significantly affect cellular attachment to VCAM-1.

Cell Migration Assay or Wound-Healing Assay

A cell migration assay was performed 48 hours after transfection with an antisense oligomer. Normal human fibroblasts were transfected with oligomers and allowed to form a monolayer. A "wound" was then created by scraping the monolayer with a pipet tip and images of the wound (gap) was taken using a microscope (Nikkon TS100) at 0 and 8 hour time points. Cells migration was analysed by comparing the size of the gap at 0 and 8 hour images using Image J (Rasband, W. S., ImageJ, U. S. National Institutes of Health, Bethesda, Md., USA). Three independent experiments were performed and an average cell migration was calculated. Data were normalised to scrambled oligomer treated samples and student t test was performed for p value.

As shown in FIG. 4, cells transfected with AO21 targeting exon 4 shows slower cell migration compared to the cells transfected with other oligomers including scrambled oligomers.

Example 2

Jurkat Cells Propagation and Nucleofection

Acute T lymphocytes leukemia cell line, Jurkat cells were maintained in RPMI-1640 medium supplemented with 10% fetal bovine serum according to the instruction from ATCC. Approximately 500,000 cells were nucleofected at 500 nM using P2 Primary Cell 4D-nucleofactor X kit S (32 RCT) (Lonza, Australia) according to the manufacturer's instructions and incubated for 2-3 days before harvesting the cells for RNA transcript analysis, Western blotting and flow cytometry.

Flow Cytometry

Jurkat cells were collected 3 days after nucleofection and washed twice with cold PBS before incubating with PE fluorophore labelled anti-human ITGA4 antibody (BD Pharmingen, Australia) at a concentration recommended by the manufacturer for 20-30 min on ice. Cells were washed once with cold PBS and analysed using Beckman Coulter Gallios flow cytometer.

Immunostaining

Jurkat cells were allowed to attach to the poly D coated coverslips for 30 min at 37° C. and fixed with iced cold methanol:acetone (1:1) for 5 min on ice. The coverslips with fixed cells were washed once with 0.2% Triton in Tris Buffered Saline (TBS-T) pH 7.6 and blocked with 10% goat serum in TBS-T for 10 min. The cells were then incubated with anti-ITGA4 antibody (Cell Signalling Technology, Inc., USA cat. No. 8440) diluted 1:200 in TBS-T for 1 h at room temperature. The coverslips were then washed 5 min three times with TBS-T and incubated with Alexa Fluor® 488 conjugated goat anti-rabbit antibody (Thermo Fisher Scientific, cat. No. A-11008) diluted 1:400 in TBS-T for 1 h at room temperature. Finally, the cells were washed twice with TBS-T for 5 min each and incubated with Hoechst 50 μg/ml in TBS-T for 5 min at room temperature before the final wash with phosphate buffered saline (PBS).

Jurkat Cells Migration

The upper side of transwell migration inserts (Polyester membrane, 3 μm pore size, 6.5 mm diameter, Corning®) were coated with 50 μl of 0.5 μg/μl recombinant human VCAM-1 (R&D systems, cat no. CD-106) for overnight at room temperature and pre-equilibrated with RPMI-1640 for 1-2 h at 37° C. Jurkat cell nucleofected with PMO for 2 days were resuspended in 100 μl of serum free PRMI-1640 medium and added to the upper compartment of the insert and 600 μl of RPMI-1640 medium supplemented with 10% FBS were added to the lower compartment. The cells were allowed to migrate for 5 h at 37° C. Cells from both top and bottom chambers were collected and stained with 2 μM calcein AM fluorescent dye (Invitrogen®, Cat. No. C1430) for 30 min and fluorescent signals were measured using a fluorescence plate reader, Beckman Coulter DTX-880 Multimode Detector (NSW, Australia) with excitation wavelength of 488 nm and emission detected at 512 nm. The percentage of cell migrated was calculated from the total fluorescent signals generated by top and bottom chamber.

Modifications of the above-described modes of carrying out the various embodiments of this invention will be apparent to those skilled in the art based on the above teachings related to the disclosed invention. The above embodiments of the invention are merely exemplary and should not be construed to be in any way limiting.

The invention claimed is:

1. An integrin alpha-4 (ITGA4) antisense oligomer comprising at least 95% sequence identity to the nucleotide sequence of SEQ ID NO: 21 or 131, wherein the antisense oligomer comprises a modified backbone structure or a modified sugar moiety.

2. The antisense oligomer of claim 1 wherein one or more nucleotides of the nucleotide sequence of the oligomer comprises a modified sugar moiety.

3. The antisense oligomer of claim 1 wherein when any uracil (U) is present in the nucleotide sequence, the uracil (U) is replaced by a thymine (T).

4. The antisense oligomer of claim 1 wherein the modification of pre-mRNA splicing results in skipping of one or more exons of the ITGA4 RNA.

5. A composition comprising
one or more antisense oligomer(s) according to claim 1, and
one or more pharmaceutically acceptable carriers and/or diluents.

6. A kit comprising the antisense oligomer of claim 1 and combinations or cocktails thereof, packaged in a suitable container, and, optionally, instructions for use.

7. The oligomer of claim 1 comprising the nucleotide sequence of SEQ ID NO: 21 or 131.

8. The antisense oligomer of claim 1, wherein the oligomer is capable of binding to a selected target on an integrin alpha-4 (ITGA4).

9. The antisense oligomer of claim 1 wherein one or more nucleotides of the oligomer is resistant to RNase H.

10. The antisense oligomer of claim 1 wherein one or more nucleotides of the oligomer is an oligomer mimetic.

11. The antisense oligomer of claim 1 wherein the antisense oligomer is further modified by chemical conjugation to a moiety.

12. The antisense oligomer of claim 1 wherein the antisense oligomer is further modified by tagging with a cell penetrating peptide.

13. A method of modifying pre-mRNA splicing in an ITGA4 gene transcript or part thereof comprising administering the antisense oligomer of claim 1.

14. A method for treating or ameliorating a disease associated with ITG4 expression comprising administering to a subject in need thereof the oligomer of claim 1.

* * * * *

UNITED STATES PATENT AND TRADEMARK OFFICE
CERTIFICATE OF CORRECTION

PATENT NO. : 10,376,536 B2  
APPLICATION NO. : 15/573184  
DATED : August 13, 2019  
INVENTOR(S) : Stephen Donald Wilton et al.

Page 1 of 1

It is certified that error appears in the above-identified patent and that said Letters Patent is hereby corrected as shown below:

On the Title Page

At item (57), Line 2, "the ITGA4" should be -- an ITGA4 --.

In the Claims

At Column 93, Line 2, "ITG4" should be -- ITGA4 --.

Signed and Sealed this
Twenty-fourth Day of March, 2020

Andrei Iancu
*Director of the United States Patent and Trademark Office*

```
                           SEQUENCE LISTING

<160> NUMBER OF SEQ ID NOS: 202

<210> SEQ ID NO 1
<211> LENGTH: 20
<212> TYPE: RNA
<213> ORGANISM: Homo sapiens

<400> SEQUENCE: 1
ucucucucuu ccaaacaagu                                                   20

<210> SEQ ID NO 2
<211> LENGTH: 20
<212> TYPE: RNA
<213> ORGANISM: Homo sapiens

<400> SEQUENCE: 2
ugauugucuc ucucuuccaa                                                   20

<210> SEQ ID NO 3
<211> LENGTH: 25
<212> TYPE: RNA
<213> ORGANISM: Homo sapiens

<400> SEQUENCE: 3
ccccaaccac ugauugucuc ucucu                                             25

<210> SEQ ID NO 4
<211> LENGTH: 25
<212> TYPE: RNA
<213> ORGANISM: Homo sapiens

<400> SEQUENCE: 4
gugaccccca accacugauu gucuc                                             25

<210> SEQ ID NO 5
<211> LENGTH: 25
<212> TYPE: RNA
<213> ORGANISM: Homo sapiens

<400> SEQUENCE: 5
aaagugugac ccccaaccac ugauu                                             25

<210> SEQ ID NO 6
<211> LENGTH: 25
<212> TYPE: RNA
<213> ORGANISM: Homo sapiens

<400> SEQUENCE: 6
cuguggacca guuccaauac cuacc                                             25

<210> SEQ ID NO 7
<211> LENGTH: 20
<212> TYPE: RNA
<213> ORGANISM: Homo sapiens

<400> SEQUENCE: 7
ccaaacaagu cuuuccacaa                                                   20
```

-continued

```
<210> SEQ ID NO 8
<211> LENGTH: 20
<212> TYPE: RNA
<213> ORGANISM: Homo sapiens

<400> SEQUENCE: 8
gucucucucu uccaaacaag                                                    20

<210> SEQ ID NO 9
<211> LENGTH: 20
<212> TYPE: RNA
<213> ORGANISM: Homo sapiens

<400> SEQUENCE: 9
ugucucucuc uuccaaacaa                                                    20

<210> SEQ ID NO 10
<211> LENGTH: 20
<212> TYPE: RNA
<213> ORGANISM: Homo sapiens

<400> SEQUENCE: 10
uugucucucu cuuccaaaca                                                    20

<210> SEQ ID NO 11
<211> LENGTH: 20
<212> TYPE: RNA
<213> ORGANISM: Homo sapiens

<400> SEQUENCE: 11
auugucucuc ucuuccaaac                                                    20

<210> SEQ ID NO 12
<211> LENGTH: 20
<212> TYPE: RNA
<213> ORGANISM: Homo sapiens

<400> SEQUENCE: 12
gauugucucu cucuuccaaa                                                    20

<210> SEQ ID NO 13
<211> LENGTH: 20
<212> TYPE: RNA
<213> ORGANISM: Homo sapiens

<400> SEQUENCE: 13
cucucucuuc caaacaaguc                                                    20

<210> SEQ ID NO 14
<211> LENGTH: 20
<212> TYPE: RNA
<213> ORGANISM: Homo sapiens

<400> SEQUENCE: 14
ucucucuucc aaacaagucu                                                    20

<210> SEQ ID NO 15
<211> LENGTH: 20
<212> TYPE: RNA
<213> ORGANISM: Homo sapiens

<400> SEQUENCE: 15
cucucuucca aacaagucuu                                                    20
```

<210> SEQ ID NO 16
<211> LENGTH: 20
<212> TYPE: RNA
<213> ORGANISM: Homo sapiens

<400> SEQUENCE: 16
ucucuuccaa acaagucuuu                                                    20

<210> SEQ ID NO 17
<211> LENGTH: 20
<212> TYPE: RNA
<213> ORGANISM: Homo sapiens

<400> SEQUENCE: 17
cucuuccaaa caagucuuuc                                                    20

<210> SEQ ID NO 18
<211> LENGTH: 25
<212> TYPE: RNA
<213> ORGANISM: Homo sapiens

<400> SEQUENCE: 18
acaagucuga auaaaauaaa aguag                                              25

<210> SEQ ID NO 19
<211> LENGTH: 25
<212> TYPE: RNA
<213> ORGANISM: Homo sapiens

<400> SEQUENCE: 19
auuuucauuc uuuauguaaa auaua                                              25

<210> SEQ ID NO 20
<211> LENGTH: 20
<212> TYPE: RNA
<213> ORGANISM: Homo sapiens

<400> SEQUENCE: 20
ccaccagugg ggagcuuauu                                                    20

<210> SEQ ID NO 21
<211> LENGTH: 25
<212> TYPE: RNA
<213> ORGANISM: Homo sapiens

<400> SEQUENCE: 21
uccauagcaa ccaccagugg ggagc                                              25

<210> SEQ ID NO 22
<211> LENGTH: 20
<212> TYPE: RNA
<213> ORGANISM: Homo sapiens

<400> SEQUENCE: 22
agcaaccacc agugggagc                                                     20

<210> SEQ ID NO 23
<211> LENGTH: 20
<212> TYPE: RNA
<213> ORGANISM: Homo sapiens

<400> SEQUENCE: 23
ggcacuccau agcaaccacc                                                    20

<210> SEQ ID NO 24
<211> LENGTH: 25
<212> TYPE: RNA
<213> ORGANISM: Homo sapiens

<400> SEQUENCE: 24
aucaaaauca ugccuuaccu ugaua                                          25

<210> SEQ ID NO 25
<211> LENGTH: 24
<212> TYPE: RNA
<213> ORGANISM: Homo sapiens

<400> SEQUENCE: 25
ccauagcaac caccaguggg gagc                                           24

<210> SEQ ID NO 26
<211> LENGTH: 23
<212> TYPE: RNA
<213> ORGANISM: Homo sapiens

<400> SEQUENCE: 26
cauagcaacc accaguggggg agc                                           23

<210> SEQ ID NO 27
<211> LENGTH: 22
<212> TYPE: RNA
<213> ORGANISM: Homo sapiens

<400> SEQUENCE: 27
auagcaacca ccagugggga gc                                             22

<210> SEQ ID NO 28
<211> LENGTH: 21
<212> TYPE: RNA
<213> ORGANISM: Homo sapiens

<400> SEQUENCE: 28
uagcaaccac caguggggag c                                              21

<210> SEQ ID NO 29
<211> LENGTH: 20
<212> TYPE: RNA
<213> ORGANISM: Homo sapiens

<400> SEQUENCE: 29
uagcaaccac caguggggag                                                20

<210> SEQ ID NO 30
<211> LENGTH: 20
<212> TYPE: RNA
<213> ORGANISM: Homo sapiens

<400> SEQUENCE: 30
auagcaacca ccagugggga                                                20

<210> SEQ ID NO 31
<211> LENGTH: 20
<212> TYPE: RNA
<213> ORGANISM: Homo sapiens

<400> SEQUENCE: 31

```
uccauagcaa ccaccagugg                                              20

<210> SEQ ID NO 32
<211> LENGTH: 20
<212> TYPE: RNA
<213> ORGANISM: Homo sapiens

<400> SEQUENCE: 32
ccauagcaac caccagugggg                                             20

<210> SEQ ID NO 33
<211> LENGTH: 25
<212> TYPE: RNA
<213> ORGANISM: Homo sapiens

<400> SEQUENCE: 33
ccauagcaac caccaguggg gagcu                                        25

<210> SEQ ID NO 34
<211> LENGTH: 25
<212> TYPE: RNA
<213> ORGANISM: Homo sapiens

<400> SEQUENCE: 34
cauagcaacc accagugggg agcuu                                        25

<210> SEQ ID NO 35
<211> LENGTH: 25
<212> TYPE: RNA
<213> ORGANISM: Homo sapiens

<400> SEQUENCE: 35
auagcaacca ccagugggga gcuua                                        25

<210> SEQ ID NO 36
<211> LENGTH: 25
<212> TYPE: RNA
<213> ORGANISM: Homo sapiens

<400> SEQUENCE: 36
uagcaaccac cagugggag cuuau                                         25

<210> SEQ ID NO 37
<211> LENGTH: 25
<212> TYPE: RNA
<213> ORGANISM: Homo sapiens

<400> SEQUENCE: 37
agcaaccacc agugggagc uuauu                                         25

<210> SEQ ID NO 38
<211> LENGTH: 25
<212> TYPE: RNA
<213> ORGANISM: Homo sapiens

<400> SEQUENCE: 38
cuccauagca accaccagug gggag                                        25

<210> SEQ ID NO 39
<211> LENGTH: 25
<212> TYPE: RNA
<213> ORGANISM: Homo sapiens

<400> SEQUENCE: 39
```

```
acuccauagc aaccaccagu gggga                                          25

<210> SEQ ID NO 40
<211> LENGTH: 25
<212> TYPE: RNA
<213> ORGANISM: Homo sapiens

<400> SEQUENCE: 40
cacuccauag caaccaccag ugggg                                          25

<210> SEQ ID NO 41
<211> LENGTH: 25
<212> TYPE: RNA
<213> ORGANISM: Homo sapiens

<400> SEQUENCE: 41
ggcacuccau agcaaccacc agugg                                          25

<210> SEQ ID NO 42
<211> LENGTH: 25
<212> TYPE: RNA
<213> ORGANISM: Homo sapiens

<400> SEQUENCE: 42
ucaaugcuga auauauaugc cugua                                          25

<210> SEQ ID NO 43
<211> LENGTH: 20
<212> TYPE: RNA
<213> ORGANISM: Homo sapiens

<400> SEQUENCE: 43
gcugaauaua uaugccugua                                                20

<210> SEQ ID NO 44
<211> LENGTH: 20
<212> TYPE: RNA
<213> ORGANISM: Homo sapiens

<400> SEQUENCE: 44
ucaaugcuga auauauaugc                                                20

<210> SEQ ID NO 45
<211> LENGTH: 25
<212> TYPE: RNA
<213> ORGANISM: Homo sapiens

<400> SEQUENCE: 45
acgccagagu uaucugugac uucac                                          25

<210> SEQ ID NO 46
<211> LENGTH: 20
<212> TYPE: RNA
<213> ORGANISM: Homo sapiens

<400> SEQUENCE: 46
acgccagagu uaucugugac                                                20

<210> SEQ ID NO 47
<211> LENGTH: 20
<212> TYPE: RNA
<213> ORGANISM: Homo sapiens
```

```
<400> SEQUENCE: 47
guaccacgcc agaguuaucu                                               20

<210> SEQ ID NO 48
<211> LENGTH: 25
<212> TYPE: RNA
<213> ORGANISM: Homo sapiens

<400> SEQUENCE: 48
gggcuaccua uagcauguga aaaua                                         25

<210> SEQ ID NO 49
<211> LENGTH: 25
<212> TYPE: RNA
<213> ORGANISM: Homo sapiens

<400> SEQUENCE: 49
guuccaauac cuaccacgau ggauc                                         25

<210> SEQ ID NO 50
<211> LENGTH: 25
<212> TYPE: RNA
<213> ORGANISM: Homo sapiens

<400> SEQUENCE: 50
gaccaguucc aauaccuacc acgau                                         25

<210> SEQ ID NO 51
<211> LENGTH: 25
<212> TYPE: RNA
<213> ORGANISM: Homo sapiens

<400> SEQUENCE: 51
gcacuccaua gcaaccacca guggg                                         25

<210> SEQ ID NO 52
<211> LENGTH: 25
<212> TYPE: RNA
<213> ORGANISM: Homo sapiens

<400> SEQUENCE: 52
aucacaauua aauccuguaa gaaaa                                         25

<210> SEQ ID NO 53
<211> LENGTH: 25
<212> TYPE: RNA
<213> ORGANISM: Homo sapiens

<400> SEQUENCE: 53
cccccaucac aauuaaaucc uguaa                                         25

<210> SEQ ID NO 54
<211> LENGTH: 25
<212> TYPE: RNA
<213> ORGANISM: Homo sapiens

<400> SEQUENCE: 54 ugggggccccc aucacaauua aaucc                                        25

<210> SEQ ID NO 55
<211> LENGTH: 26
<212> TYPE: RNA
<213> ORGANISM: Homo sapiens
```

```
<400> SEQUENCE: 55
agacaaaaag agagccaguc caguaa                                          26

<210> SEQ ID NO 56
<211> LENGTH: 25
<212> TYPE: RNA
<213> ORGANISM: Homo sapiens

<400> SEQUENCE: 56
aguaccuaaa uaacuuccaa auuuu                                           25

<210> SEQ ID NO 57
<211> LENGTH: 25
<212> TYPE: RNA
<213> ORGANISM: Homo sapiens

<400> SEQUENCE: 57
cugaauaucc uuuagaaaa gggag                                            25

<210> SEQ ID NO 58
<211> LENGTH: 25
<212> TYPE: RNA
<213> ORGANISM: Homo sapiens

<400> SEQUENCE: 58
uucuuaccuu accaaucugc ucaug                                           25

<210> SEQ ID NO 59
<211> LENGTH: 25
<212> TYPE: RNA
<213> ORGANISM: Homo sapiens

<400> SEQUENCE: 59
auguaagaua uuuaguucuu uuuca                                           25

<210> SEQ ID NO 60
<211> LENGTH: 25
<212> TYPE: RNA
<213> ORGANISM: Homo sapiens

<400> SEQUENCE: 60
gacauauuac cuuuuuaccu uucau                                           25

<210> SEQ ID NO 61
<211> LENGTH: 25
<212> TYPE: RNA
<213> ORGANISM: Homo sapiens

<400> SEQUENCE: 61
uuguggagcu ccgauagcaa caucu                                           25

<210> SEQ ID NO 62
<211> LENGTH: 20
<212> TYPE: RNA
<213> ORGANISM: Homo sapiens

<400> SEQUENCE: 62
gagcuccgau agcaacaucu                                                 20

<210> SEQ ID NO 63
<211> LENGTH: 23
<212> TYPE: RNA
```

<213> ORGANISM: Homo sapiens

<400> SEQUENCE: 63
ccaucugcac ggccauugua aau                                          23

<210> SEQ ID NO 64
<211> LENGTH: 24
<212> TYPE: RNA
<213> ORGANISM: Homo sapiens

<400> SEQUENCE: 64
uaccugugag aagguugacg agau                                         24

<210> SEQ ID NO 65
<211> LENGTH: 25
<212> TYPE: RNA
<213> ORGANISM: Homo sapiens

<400> SEQUENCE: 65
cugaagnccu ucaauucucu gaaaa                                        25

<210> SEQ ID NO 66
<211> LENGTH: 26
<212> TYPE: RNA
<213> ORGANISM: Homo sapiens

<400> SEQUENCE: 66
aucaauuugu ccugauauag acuguc                                       26

<210> SEQ ID NO 67
<211> LENGTH: 25
<212> TYPE: RNA
<213> ORGANISM: Homo sapiens

<400> SEQUENCE: 67
gauaaacuaa uuacucaccu acaua                                        25

<210> SEQ ID NO 68
<211> LENGTH: 25
<212> TYPE: RNA
<213> ORGANISM: Homo sapiens

<400> SEQUENCE: 68
uuagcaagac agcagaauca gaccg                                        25

<210> SEQ ID NO 69
<211> LENGTH: 25
<212> TYPE: RNA
<213> ORGANISM: Homo sapiens

<400> SEQUENCE: 69
agcagugaaa uauaucaguc uuacc                                        25

<210> SEQ ID NO 70
<211> LENGTH: 24
<212> TYPE: RNA
<213> ORGANISM: Homo sapiens

<400> SEQUENCE: 70
guuccauuag aagagaaaua gaau                                         24

<210> SEQ ID NO 71
<211> LENGTH: 24

<212> TYPE: RNA
<213> ORGANISM: Homo sapiens

<400> SEQUENCE: 71
uccuguaauc acgucagaag uucc                                          24

<210> SEQ ID NO 72
<211> LENGTH: 24
<212> TYPE: RNA
<213> ORGANISM: Homo sapiens

<400> SEQUENCE: 72
cauuacccgc auaaaugcuu gaug                                          24

<210> SEQ ID NO 73
<211> LENGTH: 24
<212> TYPE: RNA
<213> ORGANISM: Homo sapiens

<400> SEQUENCE: 73
acccgcauaa augcuugaug uguu                                          24

<210> SEQ ID NO 74
<211> LENGTH: 26
<212> TYPE: RNA
<213> ORGANISM: Homo sapiens

<400> SEQUENCE: 74
ugaauugggg ugaggauguc ccgcac                                        26

<210> SEQ ID NO 75
<211> LENGTH: 25
<212> TYPE: RNA
<213> ORGANISM: Homo sapiens

<400> SEQUENCE: 75
cugaugacau gaggaccaag guggu                                         25

<210> SEQ ID NO 76
<211> LENGTH: 25
<212> TYPE: RNA
<213> ORGANISM: Homo sapiens

<400> SEQUENCE: 76
gcugaagugg ugggaauucc ucugu                                         25

<210> SEQ ID NO 77
<211> LENGTH: 25
<212> TYPE: RNA
<213> ORGANISM: Homo sapiens

<400> SEQUENCE: 77
uaugucuuuu ucuuucuucu gcuga                                         25

<210> SEQ ID NO 78
<211> LENGTH: 25
<212> TYPE: RNA
<213> ORGANISM: Homo sapiens

<400> SEQUENCE: 78
aaaaaauaaa acuccuuucc ugaaa                                         25

<210> SEQ ID NO 79

-continued

```
<211> LENGTH: 20
<212> TYPE: RNA
<213> ORGANISM: Homo sapiens

<400> SEQUENCE: 79
uaugaauuaa caaaaacaag                                           20

<210> SEQ ID NO 80
<211> LENGTH: 25
<212> TYPE: RNA
<213> ORGANISM: Homo sapiens

<400> SEQUENCE: 80
gaauaaagga aaauauuccu acugu                                     25

<210> SEQ ID NO 81
<211> LENGTH: 20
<212> TYPE: RNA
<213> ORGANISM: Homo sapiens

<400> SEQUENCE: 81
uuuuaaaaau uuaguuaaau                                           20

<210> SEQ ID NO 82
<211> LENGTH: 20
<212> TYPE: RNA
<213> ORGANISM: Homo sapiens

<400> SEQUENCE: 82
acauauaguu cacuucuuca                                           20

<210> SEQ ID NO 83
<211> LENGTH: 25
<212> TYPE: RNA
<213> ORGANISM: Homo sapiens

<400> SEQUENCE: 83
aaaaaugaaa caacuguuuu ggaca                                     25

<210> SEQ ID NO 84
<211> LENGTH: 20
<212> TYPE: RNA
<213> ORGANISM: Homo sapiens

<400> SEQUENCE: 84
uaucugugac uucacaguuu                                           20

<210> SEQ ID NO 85
<211> LENGTH: 20
<212> TYPE: RNA
<213> ORGANISM: Homo sapiens

<400> SEQUENCE: 85
uguaccacgc cagaguuauc                                           20

<210> SEQ ID NO 86
<211> LENGTH: 20
<212> TYPE: RNA
<213> ORGANISM: Homo sapiens

<400> SEQUENCE: 86
uuguaccacg ccagaguuau                                           20
```

```
<210> SEQ ID NO 87
<211> LENGTH: 20
<212> TYPE: RNA
<213> ORGANISM: Homo sapiens

<400> SEQUENCE: 87
guuguaccac gccagaguua                                               20

<210> SEQ ID NO 88
<211> LENGTH: 20
<212> TYPE: RNA
<213> ORGANISM: Homo sapiens

<400> SEQUENCE: 88
aguuguacca cgccagaguu                                               20

<210> SEQ ID NO 89
<211> LENGTH: 20
<212> TYPE: RNA
<213> ORGANISM: Homo sapiens

<400> SEQUENCE: 89
aaguuguacc acgccagagu                                               20

<210> SEQ ID NO 90
<211> LENGTH: 25
<212> TYPE: RNA
<213> ORGANISM: Homo sapiens

<400> SEQUENCE: 90
ugaaacacuu acccuugaga gauga                                         25

<210> SEQ ID NO 91
<211> LENGTH: 20
<212> TYPE: RNA
<213> ORGANISM: Homo sapiens

<400> SEQUENCE: 91
ucaaguugua ccacgccaga                                               20

<210> SEQ ID NO 92
<211> LENGTH: 20
<212> TYPE: RNA
<213> ORGANISM: Homo sapiens

<400> SEQUENCE: 92
uaccacgcca gaguuaucug                                               20

<210> SEQ ID NO 93
<211> LENGTH: 20
<212> TYPE: RNA
<213> ORGANISM: Homo sapiens

<400> SEQUENCE: 93
accacgccag aguuaucugu                                               20

<210> SEQ ID NO 94
<211> LENGTH: 20
<212> TYPE: RNA
<213> ORGANISM: Homo sapiens

<400> SEQUENCE: 94
ccacgccaga guuaucugug                                               20
```

```
<210> SEQ ID NO 95
<211> LENGTH: 20
<212> TYPE: RNA
<213> ORGANISM: Homo sapiens

<400> SEQUENCE: 95
cacgccagag uuaucuguga                                              20

<210> SEQ ID NO 96
<211> LENGTH: 25
<212> TYPE: RNA
<213> ORGANISM: Homo sapiens

<400> SEQUENCE: 96
uaucuaucug uaaaacacag accag                                        25

<210> SEQ ID NO 97
<211> LENGTH: 25
<212> TYPE: RNA
<213> ORGANISM: Homo sapiens

<400> SEQUENCE: 97
gcucugcuga gugagcucac aucca                                        25

<210> SEQ ID NO 98
<211> LENGTH: 25
<212> TYPE: RNA
<213> ORGANISM: Homo sapiens

<400> SEQUENCE: 98
uuauaccagg uagcaugcac uguga                                        25

<210> SEQ ID NO 99
<211> LENGTH: 24
<212> TYPE: RNA
<213> ORGANISM: Homo sapiens

<400> SEQUENCE: 99
aaugaaguug gguuuacaaa ccug                                         24

<210> SEQ ID NO 100
<211> LENGTH: 23
<212> TYPE: RNA
<213> ORGANISM: Homo sapiens

<400> SEQUENCE: 100
caucauuuga uccauacaca aau                                          23

<210> SEQ ID NO 101
<211> LENGTH: 25
<212> TYPE: RNA
<213> ORGANISM: Homo sapiens

<400> SEQUENCE: 101
ugggcgcacc cacuaggagc cuaaa                                        25

<210> SEQ ID NO 102
<211> LENGTH: 25
<212> TYPE: RNA
<213> ORGANISM: Homo sapiens

<400> SEQUENCE: 102
ucacccagcu ggagcuguuc gcacg                                        25
```

<210> SEQ ID NO 103
<211> LENGTH: 26
<212> TYPE: RNA
<213> ORGANISM: Homo sapiens

<400> SEQUENCE: 103
caggacuugc ccuauggugg ggucca                                          26

<210> SEQ ID NO 104
<211> LENGTH: 25
<212> TYPE: RNA
<213> ORGANISM: Homo sapiens

<400> SEQUENCE: 104
uuuucacaua aucuaaaaug aaaua                                           25

<210> SEQ ID NO 105
<211> LENGTH: 24
<212> TYPE: RNA
<213> ORGANISM: Homo sapiens

<400> SEQUENCE: 105
uuugaacaau uaccuugug uaaa                                             24

<210> SEQ ID NO 106
<211> LENGTH: 25
<212> TYPE: RNA
<213> ORGANISM: Homo sapiens

<400> SEQUENCE: 106
cuccaaagua cgauccaagc ugucc                                           25

<210> SEQ ID NO 107
<211> LENGTH: 25
<212> TYPE: RNA
<213> ORGANISM: Homo sapiens

<400> SEQUENCE: 107
cacucuuccu uccucucuga uggug                                           25

<210> SEQ ID NO 108
<211> LENGTH: 25
<212> TYPE: RNA
<213> ORGANISM: Homo sapiens

<400> SEQUENCE: 108
cuuggacaua ccgagccaga guuga                                           25

<210> SEQ ID NO 109
<211> LENGTH: 25
<212> TYPE: RNA
<213> ORGANISM: Homo sapiens

<400> SEQUENCE: 109
auugcauuca uuacugcucc cuaga                                           25

<210> SEQ ID NO 110
<211> LENGTH: 25
<212> TYPE: RNA
<213> ORGANISM: Homo sapiens

<400> SEQUENCE: 110
uaccuucaaa gccaucauug ucaau                                          25

<210> SEQ ID NO 111
<211> LENGTH: 25
<212> TYPE: RNA
<213> ORGANISM: Homo sapiens

<400> SEQUENCE: 111
acuacagguc uuguccugag aagga                                          25

<210> SEQ ID NO 112
<211> LENGTH: 25
<212> TYPE: RNA
<213> ORGANISM: Homo sapiens

<400> SEQUENCE: 112
agggcauacc caccaaugua accug                                          25

<210> SEQ ID NO 113
<211> LENGTH: 25
<212> TYPE: RNA
<213> ORGANISM: Homo sapiens

<400> SEQUENCE: 113
ccuugcaaag uuuaucugga aauaa                                          25

<210> SEQ ID NO 114
<211> LENGTH: 25
<212> TYPE: RNA
<213> ORGANISM: Homo sapiens

<400> SEQUENCE: 114
aaccuguaaa ucagcagaac aauuu                                          25

<210> SEQ ID NO 115
<211> LENGTH: 25
<212> TYPE: RNA
<213> ORGANISM: Homo sapiens

<400> SEQUENCE: 115
cuuacuucaa aaacccaauc uuugc                                          25

<210> SEQ ID NO 116
<211> LENGTH: 25
<212> TYPE: RNA
<213> ORGANISM: Homo sapiens

<400> SEQUENCE: 116
uuuauuuuca uggggccuaa aaauu                                          25

<210> SEQ ID NO 117
<211> LENGTH: 23
<212> TYPE: RNA
<213> ORGANISM: Homo sapiens

<400> SEQUENCE: 117
caucaauguc uucauacucc caa                                            23

<210> SEQ ID NO 118
<211> LENGTH: 25
<212> TYPE: RNA
<213> ORGANISM: Homo sapiens

<400> SEQUENCE: 118
cuuaccagcu cuaaaaucuu aauga                                               25

<210> SEQ ID NO 119
<211> LENGTH: 25
<212> TYPE: RNA
<213> ORGANISM: Homo sapiens

<400> SEQUENCE: 119 ccauuccuc uucauuuuca cuaua                                                25

<210> SEQ ID NO 120
<211> LENGTH: 25
<212> TYPE: RNA
<213> ORGANISM: Homo sapiens

<400> SEQUENCE: 120
aggaagccuu uaugcuacu uaccc                                                25

<210> SEQ ID NO 121
<211> LENGTH: 25
<212> TYPE: RNA
<213> ORGANISM: Homo sapiens

<400> SEQUENCE: 121
gccaguguug auaaccugau aagaa                                               25

<210> SEQ ID NO 122
<211> LENGTH: 25
<212> TYPE: RNA
<213> ORGANISM: Homo sapiens

<400> SEQUENCE: 122
aauacauuuu uaccuggaca uccaa                                               25

<210> SEQ ID NO 123
<211> LENGTH: 25
<212> TYPE: RNA
<213> ORGANISM: Homo sapiens

<400> SEQUENCE: 123
guggcauucu ccaguaguag ucuau                                               25

<210> SEQ ID NO 124
<211> LENGTH: 25
<212> TYPE: RNA
<213> ORGANISM: Homo sapiens

<400> SEQUENCE: 124
accaauagcc ucuuaucagu cuugg                                               25

<210> SEQ ID NO 125
<211> LENGTH: 25
<212> TYPE: RNA
<213> ORGANISM: Homo sapiens

<400> SEQUENCE: 125
uggaucagcu uuuaugcagu acuug                                               25

<210> SEQ ID NO 126
<211> LENGTH: 26
<212> TYPE: RNA
<213> ORGANISM: Homo sapiens

```
<400> SEQUENCE: 126
uaugaacacu ggcuucuuuu ccacuu                                    26

<210> SEQ ID NO 127
<211> LENGTH: 24
<212> TYPE: RNA
<213> ORGANISM: Homo sapiens

<400> SEQUENCE: 127
uuagacuuac uuaccauuuc uaaa                                      24

<210> SEQ ID NO 128
<211> LENGTH: 25
<212> TYPE: RNA
<213> ORGANISM: Homo sapiens

<400> SEQUENCE: 128 cugaagcuc auccuguuua auaaa                                      25

<210> SEQ ID NO 129
<211> LENGTH: 25
<212> TYPE: RNA
<213> ORGANISM: Homo sapiens

<400> SEQUENCE: 129
aucuuacaug cgcaacauuc ucauc                                     25

<210> SEQ ID NO 130
<211> LENGTH: 25
<212> TYPE: RNA
<213> ORGANISM: Homo sapiens

<400> SEQUENCE: 130
uccuuccagu agaaccuacg ugagu                                     25

<210> SEQ ID NO 131
<211> LENGTH: 25
<212> TYPE: RNA
<213> ORGANISM: Homo sapiens

<400> SEQUENCE: 131
aaauaacguu ugggucuuug augau                                     25

<210> SEQ ID NO 132
<211> LENGTH: 25
<212> TYPE: RNA
<213> ORGANISM: Homo sapiens

<400> SEQUENCE: 132
cuuaccuucc acauaacaua ugaga                                     25

<210> SEQ ID NO 133
<211> LENGTH: 25
<212> TYPE: RNA
<213> ORGANISM: Homo sapiens

<400> SEQUENCE: 133
gcugaauaua uaugccugua auuag                                     25

<210> SEQ ID NO 134
<211> LENGTH: 25
<212> TYPE: RNA
<213> ORGANISM: Homo sapiens
```

```
<400> SEQUENCE: 134
ugcugaauau auaugccugu aauua                                        25

<210> SEQ ID NO 135
<211> LENGTH: 25
<212> TYPE: RNA
<213> ORGANISM: Homo sapiens

<400> SEQUENCE: 135
augcugaaua uauaugccug uaauu                                        25

<210> SEQ ID NO 136
<211> LENGTH: 25
<212> TYPE: RNA
<213> ORGANISM: Homo sapiens

<400> SEQUENCE: 136
aaugcugaau auauaugccu guaau                                        25

<210> SEQ ID NO 137
<211> LENGTH: 25
<212> TYPE: RNA
<213> ORGANISM: Homo sapiens

<400> SEQUENCE: 137
caaugcugaa uauauaugcc uguaa                                        25

<210> SEQ ID NO 138
<211> LENGTH: 25
<212> TYPE: RNA
<213> ORGANISM: Homo sapiens

<400> SEQUENCE: 138
aucaaugcug aauauauaug ccugu                                        25

<210> SEQ ID NO 139
<211> LENGTH: 25
<212> TYPE: RNA
<213> ORGANISM: Homo sapiens

<400> SEQUENCE: 139
caucaaugcu gaauauauau gccug                                        25

<210> SEQ ID NO 140
<211> LENGTH: 25
<212> TYPE: RNA
<213> ORGANISM: Homo sapiens

<400> SEQUENCE: 140
ucaucaaugc ugaauauaua ugccu                                        25

<210> SEQ ID NO 141
<211> LENGTH: 25
<212> TYPE: RNA
<213> ORGANISM: Homo sapiens

<400> SEQUENCE: 141
uucaucaaug cugaauauau augcc                                        25

<210> SEQ ID NO 142
<211> LENGTH: 25
<212> TYPE: RNA
```

```
<213> ORGANISM: Homo sapiens

<400> SEQUENCE: 142
uuucaucaau gcugaauaua uaugc                                          25

<210> SEQ ID NO 143
<211> LENGTH: 25
<212> TYPE: RNA
<213> ORGANISM: Homo sapiens

<400> SEQUENCE: 143
acgccagagu uaucugugac uucac                                          25

<210> SEQ ID NO 144
<211> LENGTH: 20
<212> TYPE: RNA
<213> ORGANISM: Homo sapiens

<400> SEQUENCE: 144
acgccagagu uaucugugac                                                20

<210> SEQ ID NO 145
<211> LENGTH: 20
<212> TYPE: RNA
<213> ORGANISM: Homo sapiens

<400> SEQUENCE: 145
guaccacgcc agaguuaucu                                                20

<210> SEQ ID NO 146
<211> LENGTH: 18
<212> TYPE: RNA
<213> ORGANISM: Homo sapiens

<400> SEQUENCE: 146
guaccacgcc agaguuau                                                  18

<210> SEQ ID NO 147
<211> LENGTH: 18
<212> TYPE: RNA
<213> ORGANISM: Homo sapiens

<400> SEQUENCE: 147
accacgccag aguuaucu                                                  18

<210> SEQ ID NO 148
<211> LENGTH: 26
<212> TYPE: RNA
<213> ORGANISM: Homo sapiens

<400> SEQUENCE: 148
acacuggcuu cuuuuccacu uuccau                                         26

<210> SEQ ID NO 149
<211> LENGTH: 26
<212> TYPE: RNA
<213> ORGANISM: Homo sapiens

<400> SEQUENCE: 149
aacacuggcu ucuuuuccac uuucca                                         26

<210> SEQ ID NO 150
<211> LENGTH: 26
```

<212> TYPE: RNA
<213> ORGANISM: Homo sapiens

<400> SEQUENCE: 150
gaacacuggc uucuuuucca cuuucc          26

<210> SEQ ID NO 151
<211> LENGTH: 26
<212> TYPE: RNA
<213> ORGANISM: Homo sapiens

<400> SEQUENCE: 151
ugaacacugg cuucuuuucc acuuuc          26

<210> SEQ ID NO 152
<211> LENGTH: 26
<212> TYPE: RNA
<213> ORGANISM: Homo sapiens

<400> SEQUENCE: 152
augaacacug gcuucuuuuc cacuuu          26

<210> SEQ ID NO 153
<211> LENGTH: 26
<212> TYPE: RNA
<213> ORGANISM: Homo sapiens

<400> SEQUENCE: 153
auaugaacac uggcuucuuu uccacu          26

<210> SEQ ID NO 154
<211> LENGTH: 26
<212> TYPE: RNA
<213> ORGANISM: Homo sapiens

<400> SEQUENCE: 154
gauaugaaca cuggcuucuu uuccac          26

<210> SEQ ID NO 155
<211> LENGTH: 26
<212> TYPE: RNA
<213> ORGANISM: Homo sapiens

<400> SEQUENCE: 155
ggauaugaac acuggcuucu uuucca          26

<210> SEQ ID NO 156
<211> LENGTH: 26
<212> TYPE: RNA
<213> ORGANISM: Homo sapiens

<400> SEQUENCE: 156
uggauaugaa cacuggcuuc uuuucc          26

<210> SEQ ID NO 157
<211> LENGTH: 26
<212> TYPE: RNA
<213> ORGANISM: Homo sapiens

<400> SEQUENCE: 157
uuggauauga acacuggcuu cuuuuc          26

<210> SEQ ID NO 158

```
<211> LENGTH: 25
<212> TYPE: RNA
<213> ORGANISM: Homo sapiens

<400> SEQUENCE: 158
ccaguagaac cuacgugagu uaaga                                          25

<210> SEQ ID NO 159
<211> LENGTH: 25
<212> TYPE: RNA
<213> ORGANISM: Homo sapiens

<400> SEQUENCE: 159
uccaguagaa ccuacgugag uuaag                                          25

<210> SEQ ID NO 160
<211> LENGTH: 25
<212> TYPE: RNA
<213> ORGANISM: Homo sapiens

<400> SEQUENCE: 160
uuccaguaga accuacguga guuaa                                          25

<210> SEQ ID NO 161
<211> LENGTH: 25
<212> TYPE: RNA
<213> ORGANISM: Homo sapiens

<400> SEQUENCE: 161
cuuccaguag aaccuacgug aguua                                          25

<210> SEQ ID NO 162
<211> LENGTH: 25
<212> TYPE: RNA
<213> ORGANISM: Homo sapiens

<400> SEQUENCE: 162
ccuuccagua gaaccuacgu gaguu                                          25

<210> SEQ ID NO 163
<211> LENGTH: 25
<212> TYPE: RNA
<213> ORGANISM: Homo sapiens

<400> SEQUENCE: 163
guccuuccag uagaaccuac gugag                                          25

<210> SEQ ID NO 164
<211> LENGTH: 25
<212> TYPE: RNA
<213> ORGANISM: Homo sapiens

<400> SEQUENCE: 164
aguccuucca guagaaccua cguga                                          25

<210> SEQ ID NO 165
<211> LENGTH: 25
<212> TYPE: RNA
<213> ORGANISM: Homo sapiens

<400> SEQUENCE: 165
uaguccuucc aguagaaccu acgug                                          25
```

```
<210> SEQ ID NO 166
<211> LENGTH: 25
<212> TYPE: RNA
<213> ORGANISM: Homo sapiens

<400> SEQUENCE: 166
guaguccuuc caguagaacc uacgu                                              25

<210> SEQ ID NO 167
<211> LENGTH: 25
<212> TYPE: RNA
<213> ORGANISM: Homo sapiens

<400> SEQUENCE: 167
uguaguccuu ccaguagaac cuacg                                              25

<210> SEQ ID NO 168
<211> LENGTH: 25
<212> TYPE: RNA
<213> ORGANISM: Homo sapiens

<400> SEQUENCE: 168
augcuuaccu uccacauaac auaug                                              25

<210> SEQ ID NO 169
<211> LENGTH: 25
<212> TYPE: RNA
<213> ORGANISM: Homo sapiens

<400> SEQUENCE: 169
ugcuuaccuu ccacauaaca uauga                                              25

<210> SEQ ID NO 170
<211> LENGTH: 25
<212> TYPE: RNA
<213> ORGANISM: Homo sapiens

<400> SEQUENCE: 170
gcuuaccuuc cacauaacau augag                                              25

<210> SEQ ID NO 171
<211> LENGTH: 25
<212> TYPE: RNA
<213> ORGANISM: Homo sapiens

<400> SEQUENCE: 171
uuaccuucca cauaacauau gagau                                              25

<210> SEQ ID NO 172
<211> LENGTH: 25
<212> TYPE: RNA
<213> ORGANISM: Homo sapiens

<400> SEQUENCE: 172
uaccuuccac auaacauaug agauc                                              25

<210> SEQ ID NO 173
<211> LENGTH: 25
<212> TYPE: RNA
<213> ORGANISM: Homo sapiens

<400> SEQUENCE: 173
accuuccaca uaacauauga gauca                                              25
```

```
<210> SEQ ID NO 174
<211> LENGTH: 25
<212> TYPE: RNA
<213> ORGANISM: Homo sapiens

<400> SEQUENCE: 174
ccuuccacau aacauaugag aucaa                                          25

<210> SEQ ID NO 175
<211> LENGTH: 24
<212> TYPE: RNA
<213> ORGANISM: Homo sapiens

<400> SEQUENCE: 175
guaguccuuc caguagaacc uacg                                           24

<210> SEQ ID NO 176
<211> LENGTH: 23
<212> TYPE: RNA
<213> ORGANISM: Homo sapiens

<400> SEQUENCE: 176
guaguccuuc caguagaacc uac                                            23

<210> SEQ ID NO 177
<211> LENGTH: 22
<212> TYPE: RNA
<213> ORGANISM: Homo sapiens

<400> SEQUENCE: 177
guaguccuuc caguagaacc ua                                             22

<210> SEQ ID NO 178
<211> LENGTH: 21
<212> TYPE: RNA
<213> ORGANISM: Homo sapiens

<400> SEQUENCE: 178
guaguccuuc caguagaacc u                                              21

<210> SEQ ID NO 179
<211> LENGTH: 20
<212> TYPE: RNA
<213> ORGANISM: Homo sapiens

<400> SEQUENCE: 179
guaguccuuc caguagaacc                                                20

<210> SEQ ID NO 180
<211> LENGTH: 24
<212> TYPE: RNA
<213> ORGANISM: Homo sapiens

<400> SEQUENCE: 180
uaguccuucc aguagaaccu acgu                                           24

<210> SEQ ID NO 181
<211> LENGTH: 23
<212> TYPE: RNA
<213> ORGANISM: Homo sapiens

<400> SEQUENCE: 181
aguccuucca guagaaccua cgu                                            23
```

```
<210> SEQ ID NO 182
<211> LENGTH: 22
<212> TYPE: RNA
<213> ORGANISM: Homo sapiens

<400> SEQUENCE: 182
guccuuccag uagaaccuac gu                                              22

<210> SEQ ID NO 183
<211> LENGTH: 21
<212> TYPE: RNA
<213> ORGANISM: Homo sapiens

<400> SEQUENCE: 183
uccuuccagu agaaccuacg u                                               21

<210> SEQ ID NO 184
<211> LENGTH: 20
<212> TYPE: RNA
<213> ORGANISM: Homo sapiens

<400> SEQUENCE: 184
ccuuccagua gaaccuacgu                                                 20

<210> SEQ ID NO 185
<211> LENGTH: 24
<212> TYPE: RNA
<213> ORGANISM: Homo sapiens

<400> SEQUENCE: 185
aauaacguuu gggucuuuga ugau                                            24

<210> SEQ ID NO 186
<211> LENGTH: 23
<212> TYPE: RNA
<213> ORGANISM: Homo sapiens

<400> SEQUENCE: 186
auaacguuug ggucuuugau gau                                             23

<210> SEQ ID NO 187
<211> LENGTH: 22
<212> TYPE: RNA
<213> ORGANISM: Homo sapiens

<400> SEQUENCE: 187
uaacguuggg gucuuugaug au                                              22

<210> SEQ ID NO 188
<211> LENGTH: 21
<212> TYPE: RNA
<213> ORGANISM: Homo sapiens

<400> SEQUENCE: 188
aacguugggg ucuuugauga u                                               21

<210> SEQ ID NO 189
<211> LENGTH: 20
<212> TYPE: RNA
<213> ORGANISM: Homo sapiens

<400> SEQUENCE: 189
```

-continued acguuugggu cuuugaugau                    20

<210> SEQ ID NO 190
<211> LENGTH: 24
<212> TYPE: RNA
<213> ORGANISM: Homo sapiens

<400> SEQUENCE: 190
aaauaacguu ugggucuuug auga               24

<210> SEQ ID NO 191
<211> LENGTH: 23
<212> TYPE: RNA
<213> ORGANISM: Homo sapiens

<400> SEQUENCE: 191
aaauaacguu ugggucuuug aug                23

<210> SEQ ID NO 192
<211> LENGTH: 22
<212> TYPE: RNA
<213> ORGANISM: Homo sapiens

<400> SEQUENCE: 192
aaauaacguu ugggucuuug au                 22

<210> SEQ ID NO 193
<211> LENGTH: 21
<212> TYPE: RNA
<213> ORGANISM: Homo sapiens

<400> SEQUENCE: 193
aaauaacguu ugggucuuug a                  21

<210> SEQ ID NO 194
<211> LENGTH: 20
<212> TYPE: RNA
<213> ORGANISM: Homo sapiens

<400> SEQUENCE: 194
aaauaacguu ugggucuuug                    20

<210> SEQ ID NO 195
<211> LENGTH: 25
<212> TYPE: RNA
<213> ORGANISM: Homo sapiens

<400> SEQUENCE: 195
gaaauaacgu uugggucuuu gauga              25

<210> SEQ ID NO 196
<211> LENGTH: 25
<212> TYPE: RNA
<213> ORGANISM: Homo sapiens

<400> SEQUENCE: 196
ugaaauaacg uuugggucuu ugaug              25

<210> SEQ ID NO 197
<211> LENGTH: 25
<212> TYPE: RNA
<213> ORGANISM: Homo sapiens

<400> SEQUENCE: 197

```
gugaaauaac guuugggucu uugau                                             25

<210> SEQ ID NO 198
<211> LENGTH: 25
<212> TYPE: RNA
<213> ORGANISM: Homo sapiens

<400> SEQUENCE: 198
ggugaaauaa cguuuggguc uuuga                                             25

<210> SEQ ID NO 199
<211> LENGTH: 25
<212> TYPE: RNA
<213> ORGANISM: Homo sapiens

<400> SEQUENCE: 199
aauaacguuu gggucuuuga ugaug                                             25

<210> SEQ ID NO 200
<211> LENGTH: 25
<212> TYPE: RNA
<213> ORGANISM: Homo sapiens

<400> SEQUENCE: 200
auaacguuug ggucuuugau gaugu                                             25

<210> SEQ ID NO 201
<211> LENGTH: 25
<212> TYPE: RNA
<213> ORGANISM: Homo sapiens

<400> SEQUENCE: 201
uaacguuugg gucuuugaug augua                                             25

<210> SEQ ID NO 202
<211> LENGTH: 25
<212> TYPE: RNA
<213> ORGANISM: Homo sapiens

<400> SEQUENCE: 202
aacguuuggg ucuuugauga uguag                                             25
```